(12) United States Patent
Martinez et al.

(10) Patent No.: US 8,919,019 B2
(45) Date of Patent: Dec. 30, 2014

(54) INTERCHANGEABLE CASES FOR BIOMETRIC MONITORING DEVICES

(71) Applicant: Fitbit, Inc., San Francisco, CA (US)

(72) Inventors: Mark Manuel Martinez, San Francisco, CA (US); Michael Hans Berlinger, San Francisco, CA (US); Keeline Burdick Wilcox, San Francisco, CA (US); Michael Joseph Francisco, Fremont, CA (US); James Park, Berkeley, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 14/213,351

(22) Filed: Mar. 14, 2014

(65) Prior Publication Data

US 2014/0200412 A1    Jul. 17, 2014

Related U.S. Application Data

(60) Division of application No. 14/027,032, filed on Sep. 13, 2013, and a continuation-in-part of application No.

(Continued)

(51) Int. Cl.
*A44C 5/00* (2006.01)
*B65D 25/22* (2006.01)
(Continued)

(52) U.S. Cl.
CPC ............... *B65D 25/22* (2013.01); *A45C 11/00* (2013.01); *B42D 15/00* (2013.01);
(Continued)

(58) Field of Classification Search
CPC .............. B42D 15/00; G09F 3/14; G09F 3/04

USPC .......... 40/633, 665, 640, 329, 636, 6, 654.01; 63/21; 224/164, 173, 171, 170, 167, 224/165, 166; 600/301

See application file for complete search history.

(56) References Cited

U.S. PATENT DOCUMENTS

| | | |
|---|---|---|
| 2,655,747 A | 10/1953 | Duskin |
| 3,381,654 A | 5/1968 | Hupp et al. |

(Continued)

FOREIGN PATENT DOCUMENTS

EP    1 721 237    8/2012

OTHER PUBLICATIONS

US Office Action, dated Jul. 11, 2014, issued in U.S. Appl. No. 14/029,764.

(Continued)

*Primary Examiner* — Syed A Islam
(74) *Attorney, Agent, or Firm* — Weaver Austin Villeneuve & Sampson

(57) ABSTRACT

A biometric monitoring device and multiple carrying cases for same are provided. In some implementations, the case may be made from a flexible viscoelastic material and the biometric monitoring device may be slipped into a receptacle in the case through an opening in the case; the opening may become distended during the insertion of the biometric monitoring device. In some implementations, the case may feature a display window that, in combination with materials of the biometric monitoring device, may mask a display of the biometric monitoring device from view when the display is off and may allow the display to be seen when the display is displaying content.

30 Claims, 27 Drawing Sheets

Related U.S. Application Data

13/767,836, filed on Feb. 14, 2013, now Pat. No. 8,543,185, which is a division of application No. 13/297,165, filed on Nov. 15, 2011, now Pat. No. 8,386,008, which is a division of application No. 13/156,304, filed on Jun. 8, 2011.

(60) Provisional application No. 61/789,454, filed on Mar. 15, 2013, provisional application No. 61/388,595, filed on Sep. 30, 2010, provisional application No. 61/390,811, filed on Oct. 7, 2010.

(51) Int. Cl.

| | | |
|---|---|---|
| *A45C 11/00* | (2006.01) | |
| *A61B 5/0205* | (2006.01) | |
| *G06F 15/00* | (2006.01) | |
| *G01C 5/06* | (2006.01) | |
| B42D 15/00 | (2006.01) | |
| G06F 3/00 | (2006.01) | |
| G09F 3/14 | (2006.01) | |
| G09F 3/04 | (2006.01) | |
| A61B 5/00 | (2006.01) | |
| A61B 5/021 | (2006.01) | |
| A61B 5/024 | (2006.01) | |
| A61B 5/08 | (2006.01) | |
| A61B 5/11 | (2006.01) | |
| A61B 5/145 | (2006.01) | |
| G01C 22/00 | (2006.01) | |

(52) U.S. Cl.
CPC .. *G06F 3/00* (2013.01); *G09F 3/14* (2013.01); *G09F 3/04* (2013.01); *A61B 5/6838* (2013.01); *A61B 5/02055* (2013.01); *A61B 5/021* (2013.01); *A61B 5/024* (2013.01); *A61B 5/0816* (2013.01); *A61B 5/1118* (2013.01); *A61B 5/14532* (2013.01); *G01C 22/006* (2013.01); *G06F 15/00* (2013.01); *A61B 2560/0214* (2013.01); *A61B 2560/0242* (2013.01); *A61B 2560/0456* (2013.01); *A61B 2562/0219* (2013.01); *A63B 2230/70* (2013.01); *G01C 5/06* (2013.01); *A61B 5/6831* (2013.01); *A61B 5/742* (2013.01); *A61B 5/002* (2013.01); *A61B 5/681* (2013.01)
USPC .................. 40/633; 40/665; 40/640; 40/329; 40/636; 40/6; 40/654.01; 63/21; 224/164; 224/173; 224/171; 224/170; 224/167; 224/165; 224/166; 600/301

(56) References Cited

U.S. PATENT DOCUMENTS

| | | | |
|---|---|---|---|
| 4,165,890 A | | 8/1979 | Leff |
| 4,415,106 A | | 11/1983 | Connell et al. |
| 4,746,043 A | | 5/1988 | Booker |
| 4,779,461 A | | 10/1988 | Gilman et al. |
| 5,511,702 A | | 4/1996 | Yang |
| 5,581,924 A | | 12/1996 | Peterson |
| 5,748,571 A * | | 5/1998 | Jackl .................. 368/282 |
| 6,213,634 B1 | | 4/2001 | Harrington et al. |
| 6,443,341 B1 | | 9/2002 | Rittmann |
| 6,583,369 B2 | | 6/2003 | Montagnino et al. |
| 6,862,827 B2 | | 3/2005 | Gregory |
| D548,457 S | | 8/2007 | Reinerio |
| 7,275,667 B2 * | | 10/2007 | Bertucci ............... 224/178 |
| D555,896 S | | 11/2007 | Ward-Llewellyn |
| 7,300,201 B2 * | | 11/2007 | Man .................. 368/282 |
| 7,490,364 B2 * | | 2/2009 | Kim .................. 2/209.13 |
| 8,250,796 B2 | | 8/2012 | Padgett et al. |
| D685,570 S | | 7/2013 | Ito et al. |
| 8,482,909 B2 | | 7/2013 | Douglas |
| 8,776,418 B1 | | 7/2014 | Martinez et al. |
| 2008/0221399 A1* | | 9/2008 | Zhou et al. .................. 600/301 |
| 2008/0265082 A1 | | 10/2008 | Angiuli |
| 2009/0265971 A1* | | 10/2009 | Cook .................. 40/633 |
| 2009/0322540 A1 | | 12/2009 | Richardson et al. |
| 2010/0229435 A1 | | 9/2010 | Diliscia et al. |
| 2010/0292599 A1 | | 11/2010 | Oleson et al. |
| 2010/0331145 A1 | | 12/2010 | Lakovic et al. |
| 2011/0032105 A1 | | 2/2011 | Hoffman et al. |
| 2011/0066009 A1 | | 3/2011 | Moon et al. |
| 2012/0061268 A1 | | 3/2012 | Turner |
| 2012/0274508 A1 | | 11/2012 | Brown et al. |
| 2013/0106684 A1 | | 5/2013 | Weast et al. |
| 2013/0162427 A1 | | 6/2013 | Dibenedetto et al. |
| 2014/0156196 A1 | | 6/2014 | Martinez et al. |
| 2014/0174958 A1 | | 6/2014 | Martinez et al. |
| 2014/0180019 A1 | | 6/2014 | Martinez et al. |
| 2014/0196539 A1 | | 7/2014 | Martinez et al. |

OTHER PUBLICATIONS

US Office Action, dated Jul. 2, 2014, issued in U.S. Appl. No. 14/027,016.
US Office Action, dated Feb. 26, 2014, issued in U.S. Appl. No. 14/027,032.
US Notice of Allowance, dated May 8, 2014, issued in U.S. Appl. No. 14/027,032.
US Office Action, dated May 28, 2014, issued in U.S. Appl. No. 14/213,336.
"Activator is One of the Best Cydia iPhone Hacks | Control your iPhone with Gestures," iphone-tips-and-advice.com, [retrieved on Jul. 9, 2013 at http://www.iphone-tips-and-advice.com/activatior. html], 10 pp.
Chudnow, Alan (Dec. 3, 2012) "Basis Wristband Make Its Debut," *The Wired Self, Living in a Wired World*, published in Health [retrieved on Jul. 22, 2013 at http://thewiredself.com/health/basis-wrist-band-make-its-debut/], 3pp.
DesMarais, Christina (posted on Sep. 3, 2013) "Which New Activity Tracker is Best for You?" *Health and Home, Health & Fitness , Guides & Reviews*, [Retrieved on Sep. 23, 2013 at http://www.techlicious.com/guide/which-new-activity-tracker-is-right-for-you/] 4 pp.
Empson, Rip, (Sep. 22, 2011) "Basis Reveals an Awesome New Affordable Heart and Health Tracker You Can Wear on Your Wrist," [retrieved on Sep. 23, 2013 at http://techcrunch.com/2011/09/22/basis-reveals-an-awesome-new . . . ], 3 pp.
Fitbit User's Manual, Last Updated Oct. 22, 2009, 15 pages.
Forerunner® 10 Owner's Manual (Aug. 2012), Garmin Ltd., 10 pp.
Forerunner® 110 Owner's Manual, (2010) "GPS-Enabled Sport Watch," Garmin Ltd., 16 pp.
Forerunner® 201 personal trainer owner's manual, (Feb. 2006) Garmin Ltd., 48 pp.
Forerunner® 205/305 Owner's Manual, GPS-enabled trainer for runners, (2006-2008), Garmin Ltd., 80 pp.
Forerunner® 210 Owner's Manual, (2010) "GPS-Enabled Sport Watch," Garmin Ltd., 28 pp.
Forerunner® 301 personal trainer owner's manual, (Feb. 2006) Garmin Ltd., 66 pp.
Forerunner® 310XT Owner's Manual, Multisport GPS Training Device, (2009-2013), Garmin Ltd., 56 pp.
Forerunner® 405 Owner's Manual, (Mar. 2011) "GPS-Enabled Sport Watch With Wireless Sync," Garmin Ltd., 56 pp.
Forerunner® 405CX Owner's Manual, "GPS-Enabled Sports Watch With Wireless Sync," (Mar. 2009), Garmin Ltd., 56 pp.
Forerunner® 410 Owner's Manual, (Jul. 2012) "GPS-Enabled Sport Watch With Wireless Sync," Garmin Ltd., 52 pp.
Forerunner® 50 with ANT+Sport™ wireless technology, Owner's Manual, (Nov. 2007) Garmin Ltd., 44 pp.
Forerunner® 910XT Owner's Manual, (Jan. 2013) Garmin Ltd., 56 pp.
Garmin Swim™ Owner's Manual (Jun. 2012), 12 pp.
Lark/Larkpro, User Manual, (2012) "What's in the box," *Lark Technologies*, 7 pp.
Larklife, User Manual, (2012) *Lark Technologies*, 7 pp.

(56) References Cited

OTHER PUBLICATIONS

Nike+ FuelBand GPS Manual, User's Guide (Product Release Date Unknown, downloaded Jul. 22, 2013), 26 pages.

Nike+SportBand User's Guide, (Product Release Date Unknown, downloaded Jul. 22, 2013), 36 pages.

Nike+SportWatch GPS Manual, User's Guide, Powered by TOMTOM, (Product Release Date Unknown, downloaded Jul. 22, 2013), 42 pages.

"Parts of Your Band," (Product Release Date Unknown, downloaded Jul. 22, 2013) Jawbone UP Band, 1 page.

Polar WearLink® + Coded Transmitter 31 Coded Transmitter W.I.N.D. User Manual, POLAR® Listen to Your Body, *Manufactured by Polar Electro Oy*, 11 pages.

Rainmaker, (Jun. 25, 2012, updated Feb. 16, 2013) "Garmin Swim watch In-Depth Review," [retrieved on Sep. 9, 2013 at http://www.dcrainmaker.com/2012/06/garmin-swim-in-depth-review.html, 38 pp.

\* cited by examiner

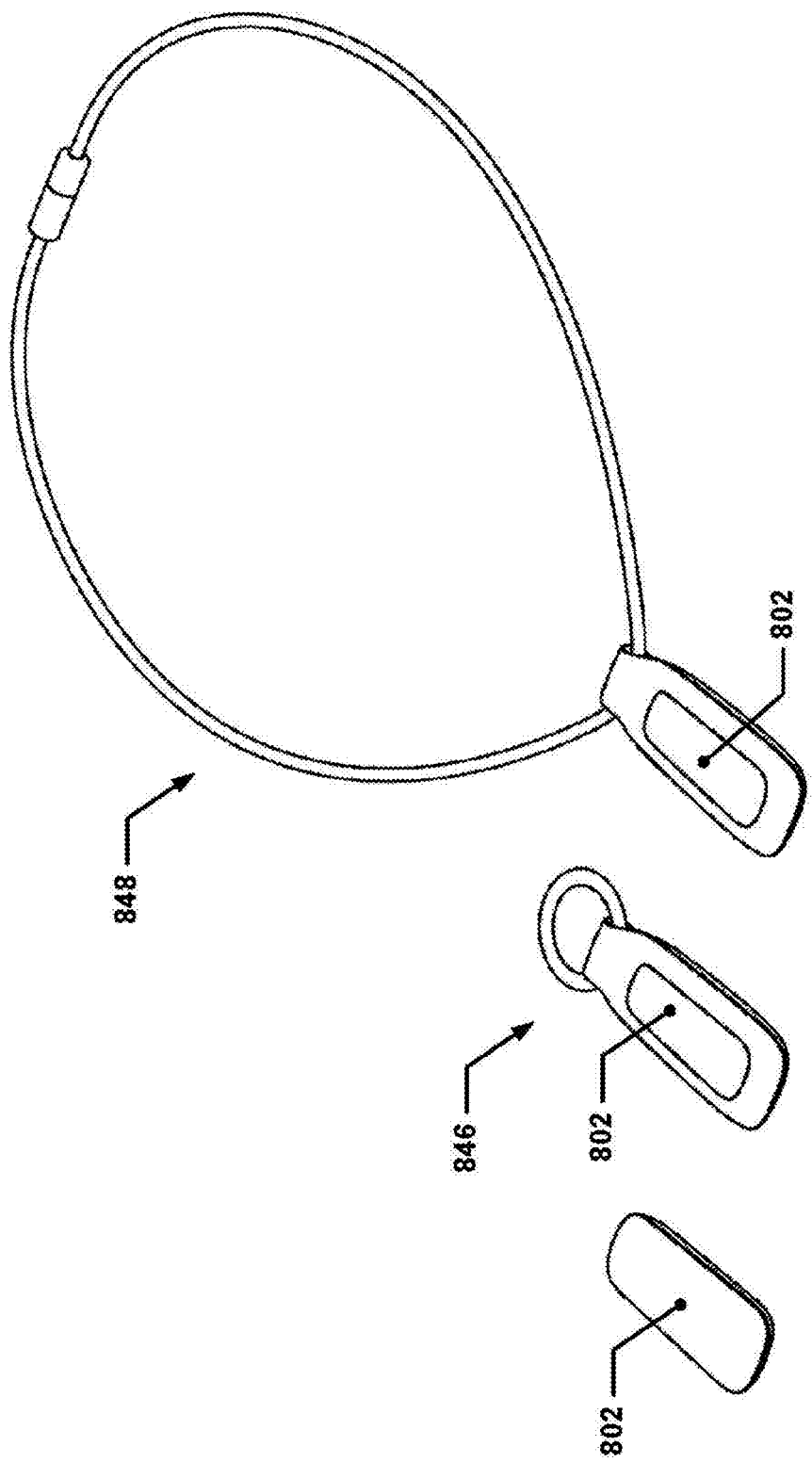

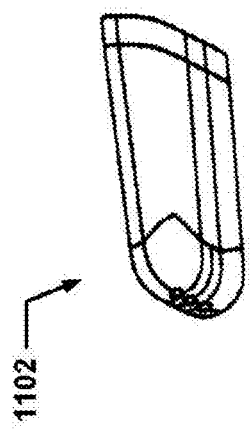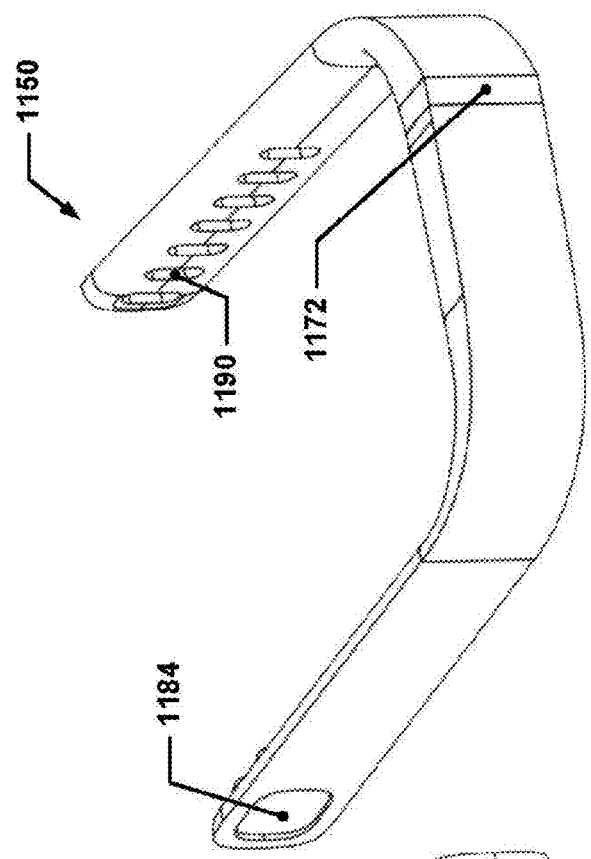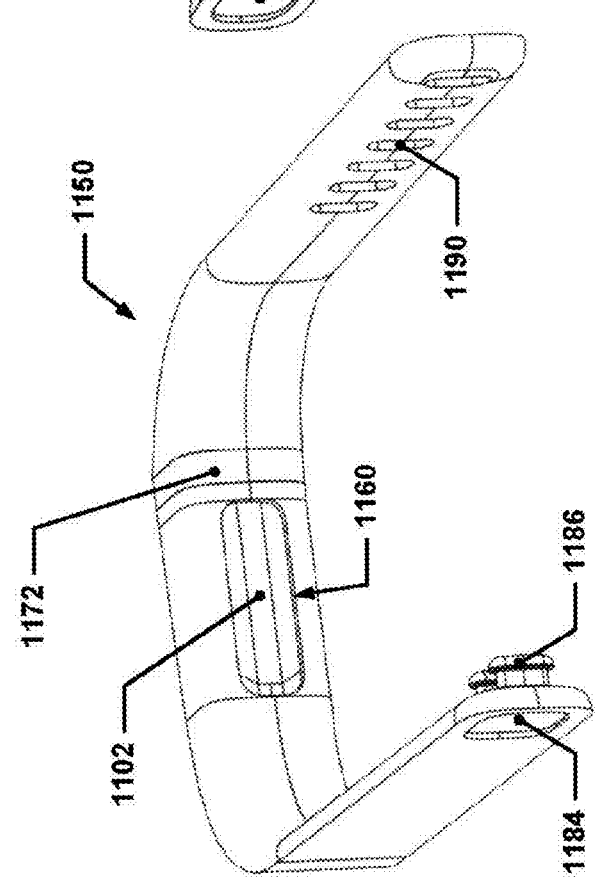

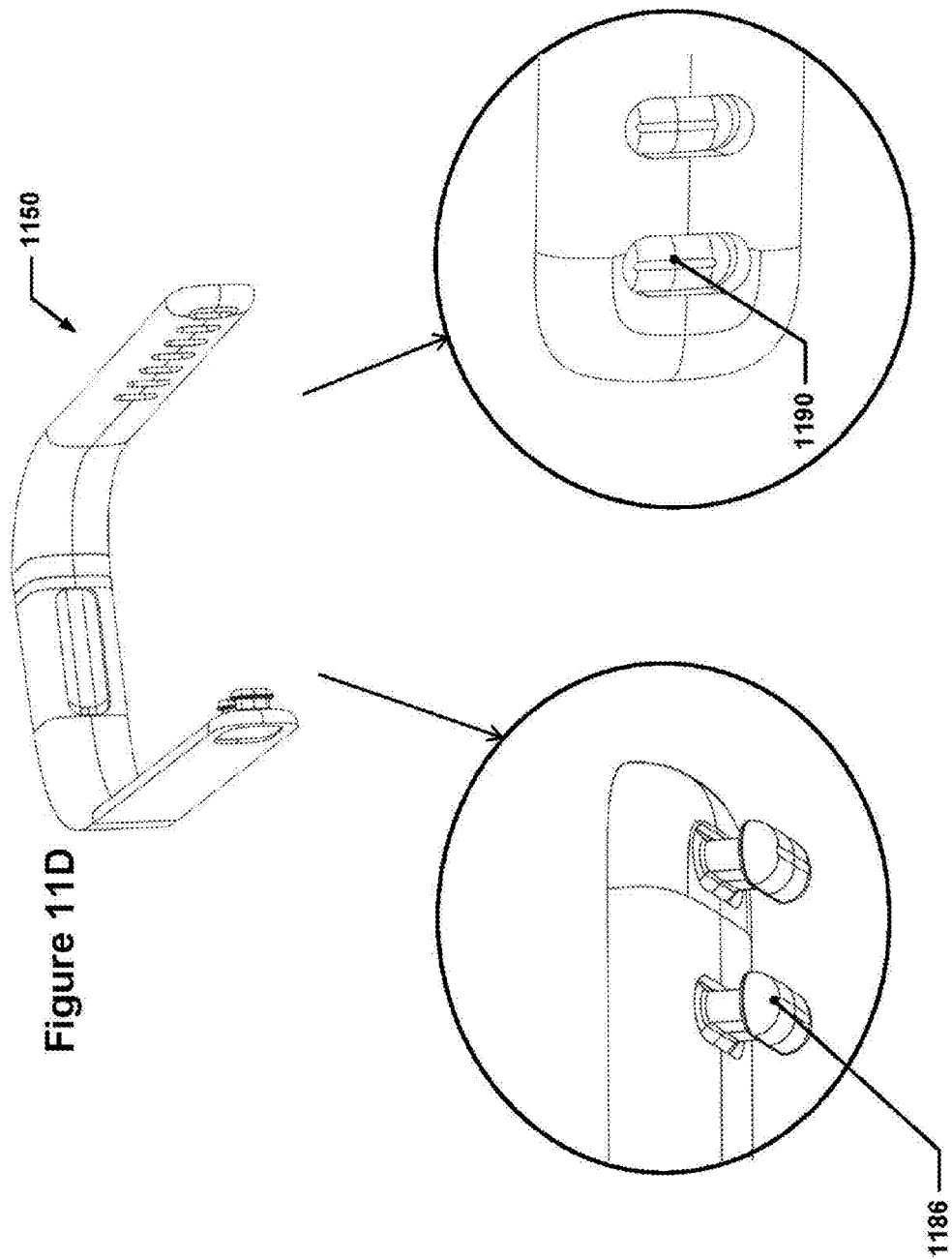

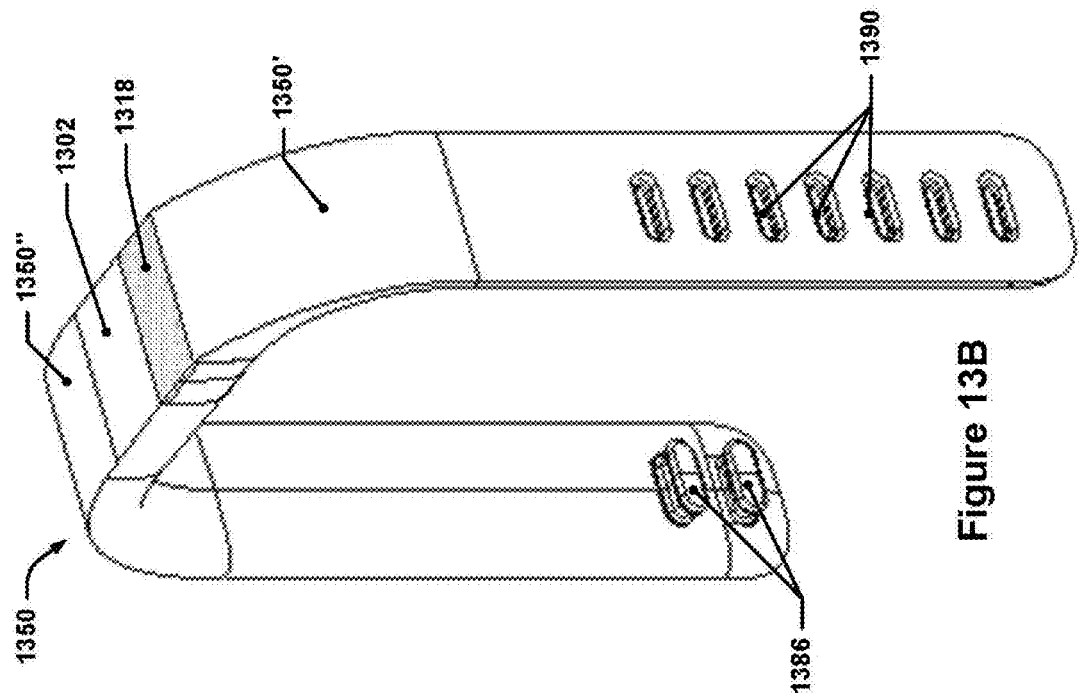
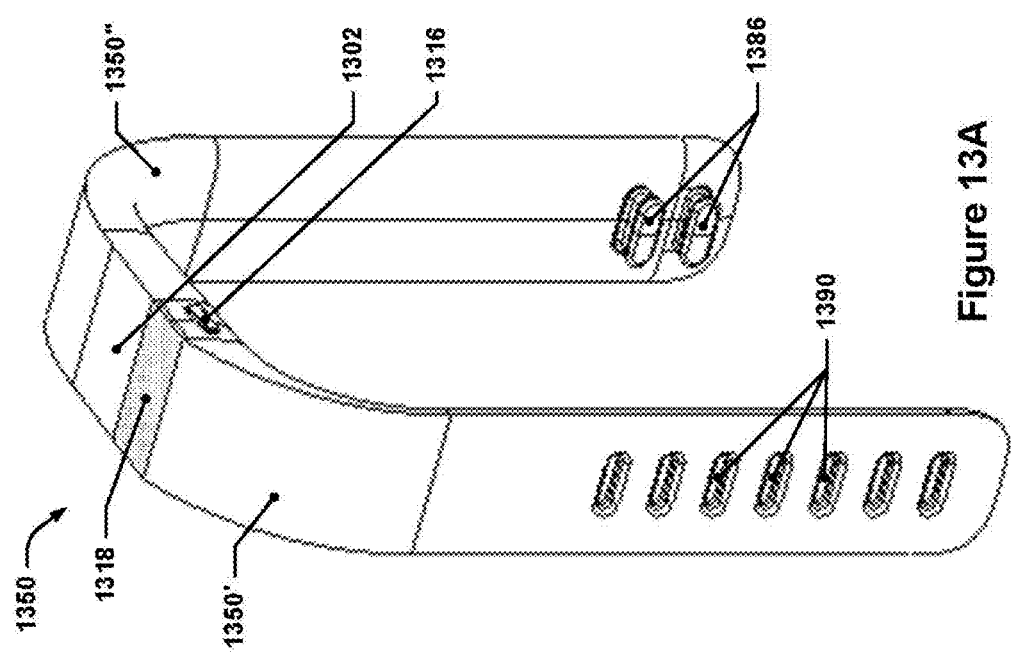
Figure 13A
Figure 13B

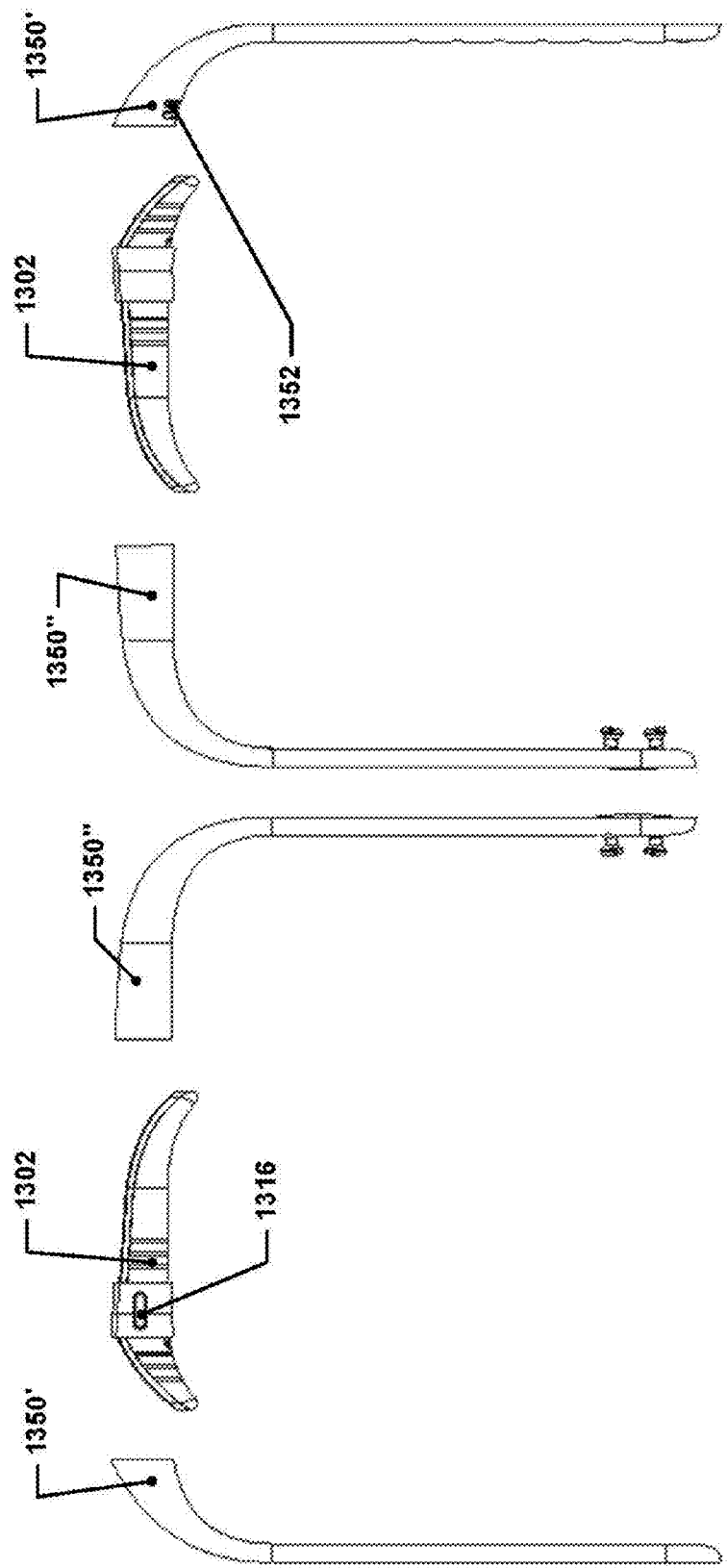

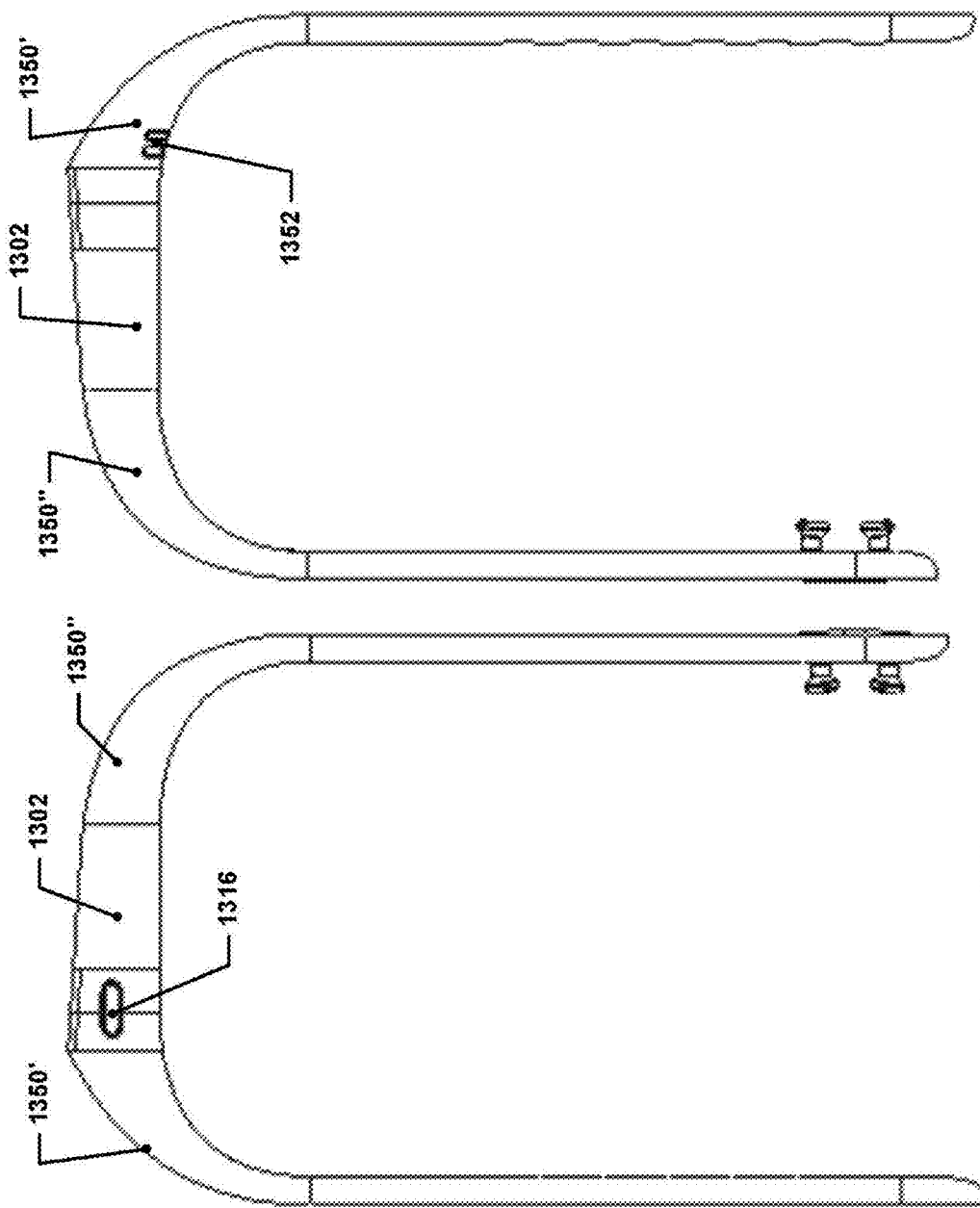

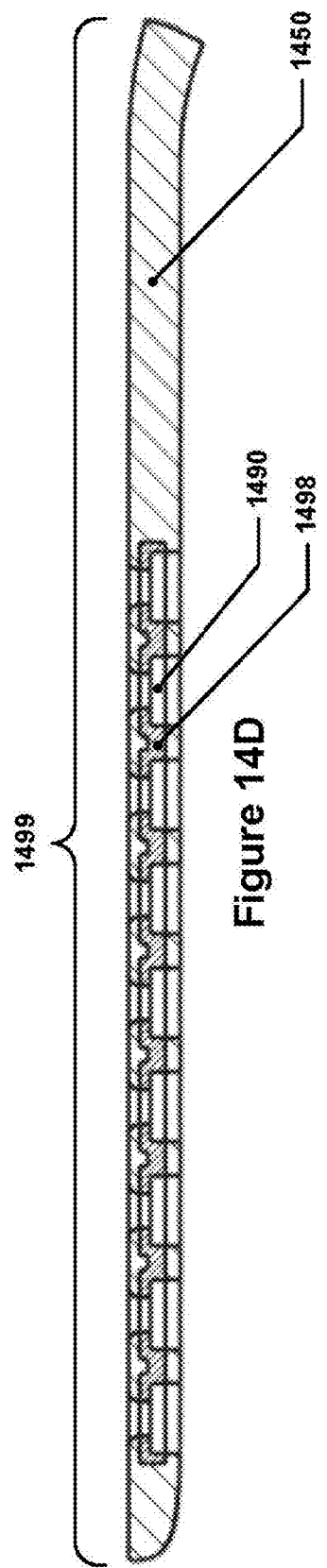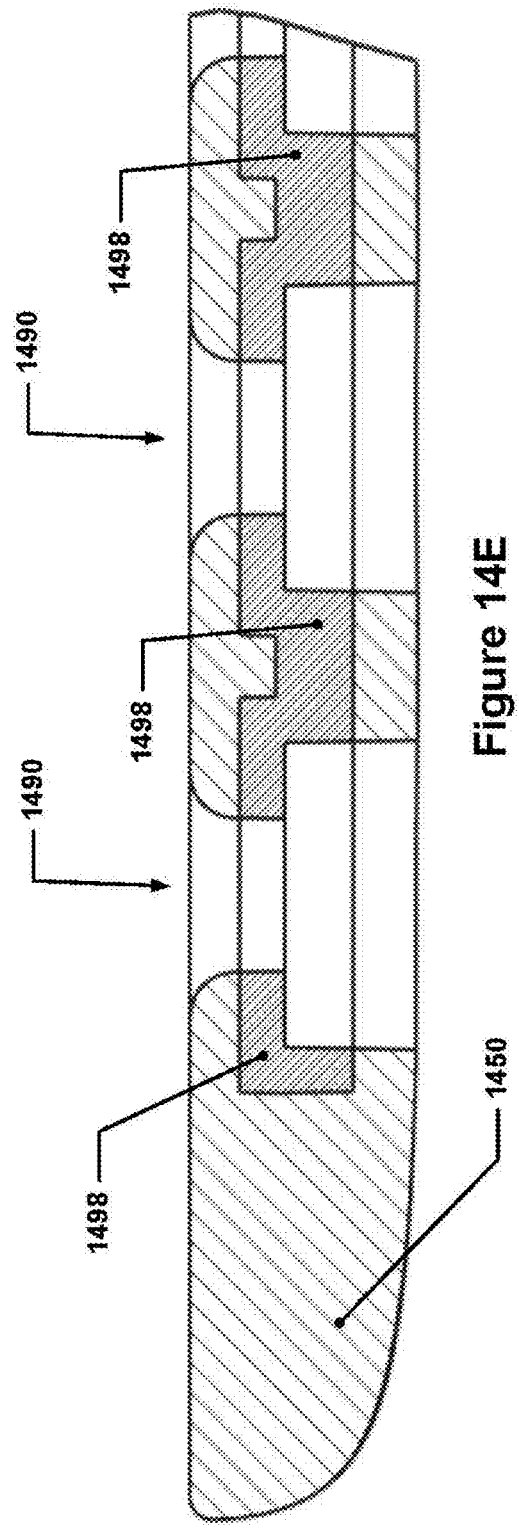

INTERCHANGEABLE CASES FOR BIOMETRIC MONITORING DEVICES

CROSS REFERENCE TO RELATED APPLICATIONS

This application is a divisional of U.S. patent application Ser. No. 14/027,032, filed Sep. 13, 2013, which itself claims benefit under 35 U.S.C. §119(e) to U.S. Provisional Application No. 61/789,454, filed Mar. 15, 2013, titled "WEARABLE BIOMETRIC MONITORING DEVICES, INTERCHANGEABLE ACCESSORIES AND INTEGRATED FASTENINGS TO PERMIT WEAR," and also claims priority as a continuation-in-part under 35 U.S.C. §120 to U.S. patent application Ser. No. 13/767,836, filed Feb. 14, 2013 and which will issue as U.S. Pat. No. 8,543,185 on Sep. 24, 2013, which is itself a divisional of U.S. patent application Ser. No. 13/297,165, filed Nov. 15, 2011 and which issued as U.S. Pat. No. 8,386,008 on Feb. 26, 2013, which is itself a divisional of U.S. patent application Ser. No. 13/156,304, filed Jun. 8, 2011, which itself claims benefit under 35 U.S.C. §119(e) to U.S. Patent Application Nos. 61/388,595 and 61/390,811, respectively filed on Sep. 30, 2010, and Oct. 7, 2010, all of which are hereby incorporated by reference herein in their entireties.

BACKGROUND

Recent consumer interest in personal health has led to a variety of personal health monitoring devices being offered on the market. Such devices, until recently, tended to be complicate to use and were typically designed for use with one activity, e.g., bicycle trip computers.

Recent advances in sensor, electronics, and power source miniaturization have allowed the size of personal health monitoring devices, also referred to herein as "biometric tracking" or "biometric monitoring" devices, to be shrunk to extremely small sizes. For example, the Fitbit Ultra is a biometric tracking device that is approximately 2" long, 0.75" wide, and 0.5" deep; it has a display, battery, sensors, wireless communications capability, power source, and interface button, as well as an integrated clip, packaged within this small volume.

SUMMARY

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale unless specifically indicated as being scaled drawings.

In some implementations, a biometric tracking system may be provided. The biometric tracking system may include a biometric tracking module having a housing with a nominal maximum dimension, at least one biometric sensor, at least one processor, a memory, and a display. The at least one biometric sensor, the at least one processor, and the display may be communicatively connected with one another and the memory may store instructions for controlling the at least one processor to: obtain biometric data from the at least one biometric sensor, receive a request to display an aspect of the biometric data on the display, cause, responsive to the request, the display to show the aspect of the biometric data on the display, and cause, when the display is in an off state, the display to turn on to show the aspect of the biometric data on the display. The biometric tracking system may also include a molded band configured to be worn on an organism's limb or neck, the molded band having a receptacle with an opening having a nominal maximum dimension smaller than the nominal maximum dimension of the housing. The biometric tracking module may be configured to be removably inserted into the receptacle via the opening.

In some implementations, the organism's limb or neck may be a person's forearm. In some such implementations, the organism's limb or neck may be a feline or canine neck.

In some implementations, the receptacle may have an interior surface spanning opposing ends of the opening that are located along an axis substantially perpendicular to the organism's limb or the neck when the molded band is worn on the organism's limb or neck, the housing may have an exterior surface, and substantially all of the interior surface between the opposing ends of the opening may contact the exterior surface when the biometric tracking module is inserted into the receptacle.

In some implementations, the receptacle may have an interior surface, the housing may have an exterior surface, and substantially all of the interior surface may contact the exterior surface when the biometric tracking module is inserted into the receptacle.

In some implementations, the molded band may be at least partially made from a compliant material between opposing ends of the opening that are located along an axis substantially perpendicular to the organism's limb or neck when the molded band is worn on the organism's limb or neck, and the molded band may be constructed such that the opening may be elastically stretched to a stretched maximum dimension larger than the nominal maximum dimension of the opening as the biometric tracking module is inserted through the opening and into the receptacle. In some such implementations, the compliant material may have a Young's modulus between about 1 MPa and 690 MPa. In some alternative or additional such implementations, the compliant material may be a thermoplastic polyurethane, a thermoplastic elastomer, a thermoplastic vulcanizate, a polyurethane, a silicone, or a combination thereof.

In some implementations, the opening may face towards the organism's limb or neck when the molded band is worn on the organism's limb or neck. In some additional or alternative implementations, the opening may face away from the organism's limb or neck when the molded band is worn on the organism's limb or neck.

In some implementations, the display may be an illuminable display and a portion of the molded band that overlays the illuminable display when the biometric tracking module is inserted into the receptacle may be made of a material that, in combination with any materials of the biometric tracking module interposed between the portion and the illuminable display when the biometric tracking module is inserted into the receptacle, has an opacity (i) that causes the illuminable display to not be visible through the portion when the biometric tracking module is inserted into the receptacle and the illuminable display is in an off state or is not displaying content and (ii) that causes the illuminable display to be visible through the portion when the biometric tracking module is inserted into the receptacle and the illuminable display is in an on state and displaying content.

In some such implementations, the portion of the molded band may be made from a tinted translucent material. In some such implementations, the tinted translucent material may have a light transmittance of between 15% and 50%.

In some implementations, the portion of the molded band may be made from a frosted translucent material. In some implementations, the portion of the molded band may have a reflective coating through which the illuminable display is visible when the biometric tracking module is inserted into the receptacle and the illuminable display is displaying content.

In some implementations, the molded band may have a first strap extending away from a first edge of the opening by a first length and a second strap extending away from a second edge of the opening on an opposite side of the opening from the first edge by a second length. The first strap, the second strap, and the receptacle substantially may define a band plane that is substantially perpendicular to a limb axis of the organism's limb or a neck axis of the organism's neck when the molded band is worn on the organism's limb or neck, and the first strap may have a plurality of similarly-sized holes distributed along at least a portion of the first length. At least one peg may protrude from the second strap, the at least one peg having a head portion and a stem portion. The head portion and the stem portion of each peg may be sized to be insertable through one of the similarly-sized holes, and each similarly-sized hole may be sized such that the similarly-sized hole is distended to a greater degree by the insertion of the head portion through the similarly-sized hole than by the insertion of the stem portion through the similarly-sized hole.

In some implementations, the biometric tracking system may include a peg component, the peg component having a base and at least one peg protruding from the base. The molded band may have a first strap extending away from a first edge of the opening by a first length and a second strap extending away from a second edge of the opening on an opposite side of the opening from the first edge by a second length. The first strap, the second strap, and the receptacle substantially may define a band plane that is substantially perpendicular to a limb axis of the organism's limb or a neck axis of the organism's neck when the molded band is worn on the organism's limb or neck. The first strap may have a plurality of first holes distributed along at least a portion of the first length, and the second strap may have a corresponding second hole for each peg of the peg component. Each peg of the peg component may have a head portion and a stem portion; the head portion and the stem portion of each peg may be sized to be insertable through one of the first holes and through the corresponding second hole, and each first hole may be sized such that the first hole is distended to a greater degree by the insertion of the head portion through the first hole than by the insertion of the stem portion through the first hole.

In some implementations, a band may be provided. The band may be configured to be worn on an organism's limb or neck and may include a molded body, a first molded strap extending away from a first end of the molded body, a second molded strap extending away from a second end of the molded body opposite the first end. The molded body, the first molded strap, and the second molded strap may be configured to substantially encircle the organism's limb or neck and may substantially define a band plane perpendicular to a limb axis of the organism's limb or a neck axis of the organism's neck when the band is worn on the organism's limb or neck. The band may also include a cavity within the molded body, the cavity sized to receive a biometric tracking device and to hold the biometric tracking device substantially fixed with respect to the molded body when the biometric tracking device is fully inserted into the cavity, and an opening in the molded body leading to the cavity, the opening sized to be smaller in cross-sectional area than the maximum cross-sectional area of the biometric tracking device in a plane substantially parallel to the opening when the biometric tracking device is fully inserted into the cavity.

In some such implementations, the organism's limb or neck may be a person's forearm. In some other such implementations, the organism's limb or neck may be a feline or canine neck.

In some implementations, the cavity may have an interior surface spanning between opposing ends of the opening, the opposing ends of the opening may be located along an axis spanning between the first end of the molded body and the second end of the molded body, and substantially all of the interior surface spanning between the opposing ends of the opening may contact an exterior surface of the biometric tracking device when the biometric tracking device is fully inserted into the cavity.

In some implementations, the cavity may have an interior surface and substantially all of the interior surface may contact an exterior surface of the biometric tracking module when the biometric tracking module is inserted into the cavity.

In some implementations, the molded body may be at least partially made from a compliant material between the first end of the molded body and the second end of the molded body, and the molded body may be designed such that the opening may be elastically stretched to permit the biometric tracking device to be fully inserted into the cavity.

In some such implementations, the compliant material may be a thermoplastic polyurethane, a thermoplastic elastomer, a thermoplastic vulcanizate, a polyurethane, a silicone, or a combination thereof. In some such implementations, the compliant material may have a Young's modulus between about 1 MPa and 690 MPa.

In some implementations, the display may be an illuminable display and a portion of the molded body that overlays the illuminable display of the biometric tracking module when the biometric tracking module is fully inserted into the cavity may be made of a material that, in combination with any materials of the biometric tracking module interposed between the portion and the illuminable display when the biometric tracking module is fully inserted into the cavity, has an opacity that causes the illuminable display to not be visible through the portion when the biometric tracking module is inserted into the cavity and the illuminable display is in an off state or is not displaying content and that causes the illuminable display to be visible through the portion when the biometric tracking module is inserted into the cavity and the illuminable display is in an on state and displaying content.

In some such implementations, the portion of the molded band may be made from a tinted translucent material, a frosted translucent material, or a reflective material. In some such implementations, the tinted translucent material may have a light transmittance of between 15% and 50%.

In some implementations, the opening may face towards the organism's limb or neck when the molded band is worn on the organism's limb or neck. In some other implementations the opening may face away from the organism's limb or neck when the molded band is worn on the organism's limb or neck.

In some implementations, a band configured to be worn on a person's limb may be provided. The band may include a pocket region having a pocket. The pocket may be formed between a first layer of flexible material and a second layer of flexible material and sized to allow a biometric tracking device associated with the band to be fully inserted within the pocket. The band may also include a slit in an exterior textile layer of the band. The slit may extend in a direction substantially parallel to the person's limb when the band is worn on the person's limb, may be shorter in length than a longest dimension of the associated biometric tracking device, and may permit the biometric tracking device to be fully inserted into the pocket. The first layer of flexible material may be a mesh through which a display on the biometric tracking device is at least partially visible when the biometric tracking device is fully inserted into the pocket with the display facing the first layer and displaying content on the display.

In some implementations, the band may be contiguous and may be configured to stretch such that the band may be slid over the person's hand and onto the person's forearm or over the person's foot and onto the person's leg before relaxing into a less-stretched configuration around the person's forearm or leg.

In some implementations, the band may also include a first end and a second end, the first end located opposite the second end. The pocket region may be located between the first end and the second end.

In some implementations the band may include a torsional flat spring element spanning between the first end and the second end. The torsional flat spring element may have a first mechanically stable configuration that causes the band to maintain a circular shape.

In some implementations, the torsional flat spring element may be mechanically bistable and may have a second mechanically stable configuration that causes the band to maintain a substantially flat shape.

In some implementations, the band may also include a first fastening region adjacent to the first end and a second fastening region adjacent to the second end and configured to engage with at least a portion of the first fastening region in a disengageable manner to allow the band to be placed around the person's limb and the first end and the second end to be connected to one another. The pocket region may be further located between the first fastening region and the second fastening region.

In some implementations, the first fastening region and the second fastening region may each include complementary fasteners such as hook-and-loop fasteners, buckle and tang fasteners, magnetic fasteners, friction clasps, camlock and strap buckles, or hook clasp fasteners.

In some implementations, the band may include a first perforated region partially or wholly overlapping with the first fastening region. The hole features that pass through the band may be distributed throughout the first perforated region.

In some implementations, the pocket may not extend into the hook region and may not extend into the loop region.

In some implementations, the band may also include a second perforated region between the second end of the band and the pocket region. The hole features passing through the band may be distributed throughout the second perforated region.

In some implementations, the slit may span between two through-holes in the exterior textile layer, and both sides of the textile layer may be coated with an elastomeric material in a localized region around the slit.

In some implementations, the exterior textile layer may have an opening substantially corresponding in size to the pocket, and the first layer of flexible material may be interposed between the exterior textile layer and the second layer of flexible material.

In some implementations, a wearable case for a biometric monitoring device may be provided. The wearable case may include a molded body made of a compliant material; a cavity within the molded body, the cavity sized to receive a biometric tracking device and to hold the biometric tracking device substantially fixed with respect to the molded body when the biometric tracking device is fully inserted into the cavity; an opening in the molded body leading to the cavity, the opening sized to be smaller in cross-sectional area than the maximum cross-sectional area of the biometric tracking device in a plane substantially parallel to the opening when the biometric tracking device is fully inserted into the cavity; and a hole that passes through the molded body and is positioned such that a keyring may pass through the hole or such that a lanyard may be threaded through the hole.

In some implementations, the wearable case may further include a lanyard threaded through the hole, the lanyard sized so as to be wearable around a person's neck. In some other implementations of the wearable case, the wearable case may also include a keyring threaded through the hole. In some implementations, the compliant material may have a Young's modulus between about 1 MPa and 690 MPa. In some implementations, the compliant material may be a thermoplastic polyurethane, a thermoplastic elastomer, a thermoplastic vulcanizate, a polyurethane, a silicone, or a combination thereof.

These and other implementations are described in further detail with reference to the Figures and the detailed description below.

BRIEF DESCRIPTION OF THE DRAWINGS

The various implementations disclosed herein are illustrated by way of example, and not by way of limitation, in the figures of the accompanying drawings, in which like reference numerals refer to similar elements.

FIGS. 6A, 6B, and 6C depict various views of an example of a portable biometric monitoring device case having a clip.

FIG. 8 depicts two different example cases for a depicted example portable biometric monitoring device.

FIG. 11A depicts an example of a portable biometric monitoring device.

FIGS. 11B and 11C depict different views of an example wristband case that may be used to house the example portable biometric monitoring device of FIG. 11A.

FIG. 11D depicts an off-angle view of the example wristband case of FIGS. 11B and 11C.

FIGS. 11E and 11F depict detail views of the ends of the bands of the example wristband case of FIG. 11D.

FIGS. 13A and 13B depict different off-angle views of another example of a portable biometric monitoring device.

FIGS. 13G and 13H depict exploded side views of the example portable biometric monitoring device shown in FIG. 13A.

FIGS. 13I and 13J depict side views of the example portable biometric monitoring device shown in FIG. 13A.

FIG. 14D depicts a cross-section of an example of a spine co-molded into a strap.

FIG. 14E depicts a detail view of the cross-section of FIG. 14D.

FIGS. 2A-8, 6A-6C, 9A, 9B, and 11A-14F are drawn to-scale within each Figure, although not necessarily from Figure to Figure.

DETAILED DESCRIPTION

Figure 9A:
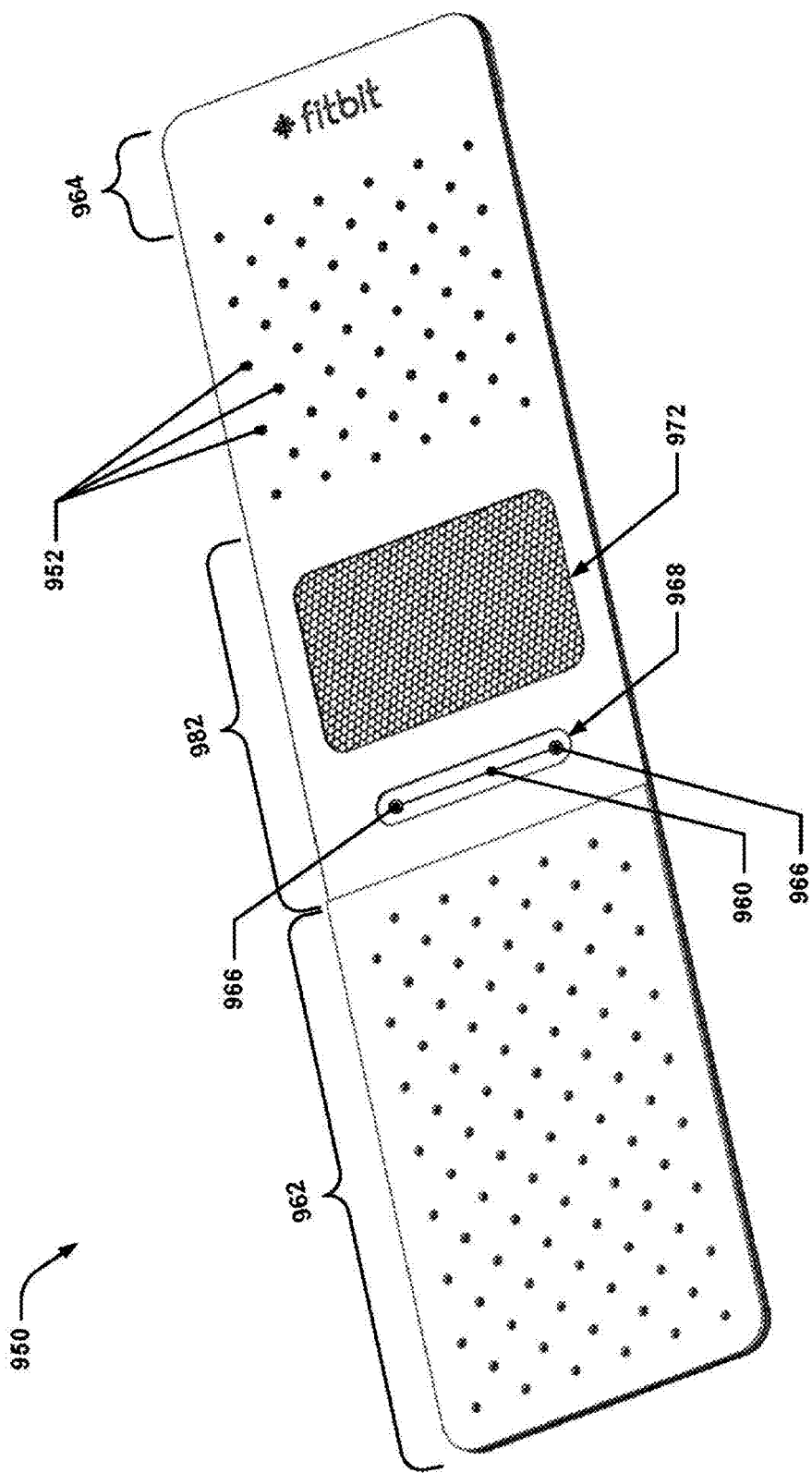
FIG. 9A depicts one example of a wristband case for a portable biometric monitoring device.
Figure 9B:
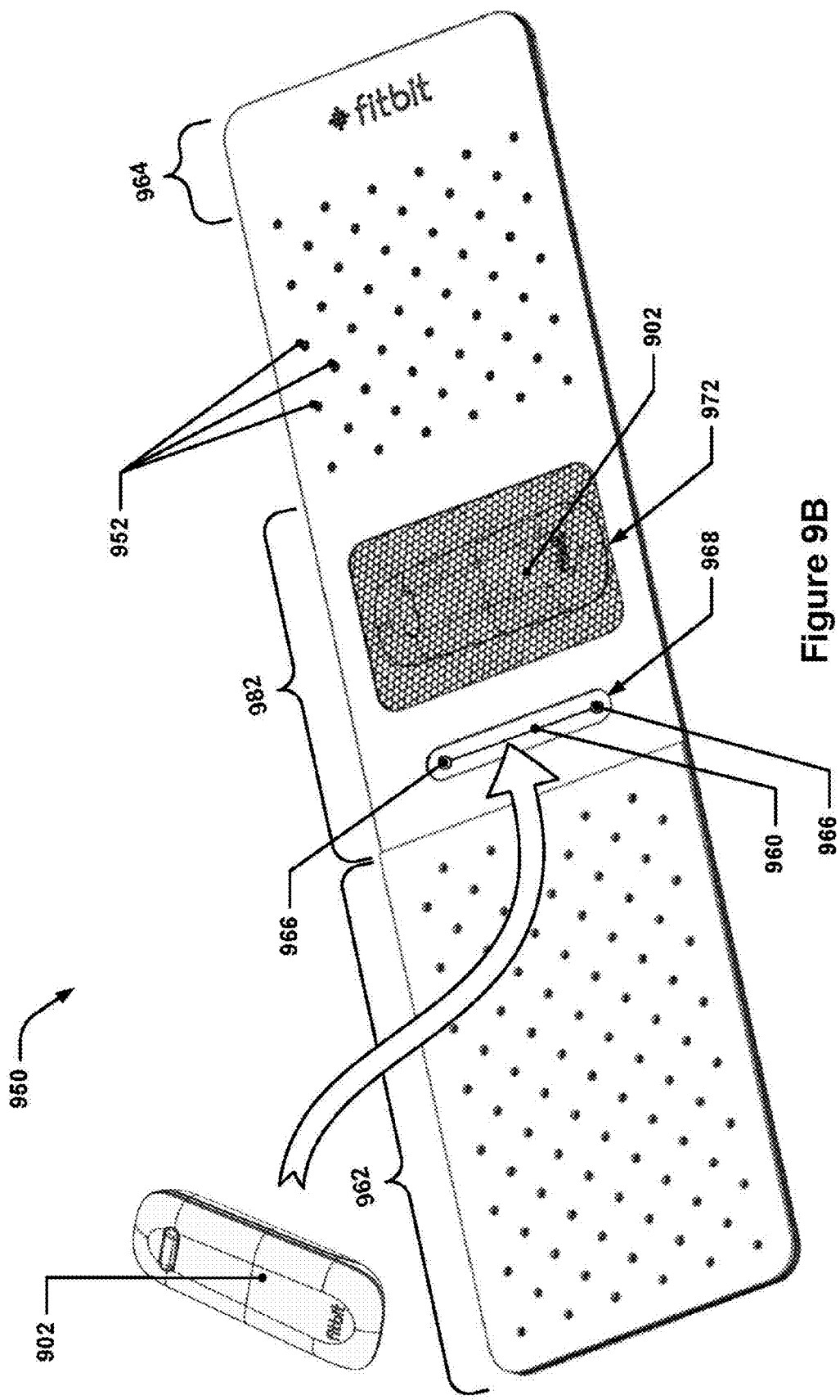
FIG. 9B depicts the example wristband case of FIG. 9A with a portable biometric monitoring device inserted.
Figure 10:
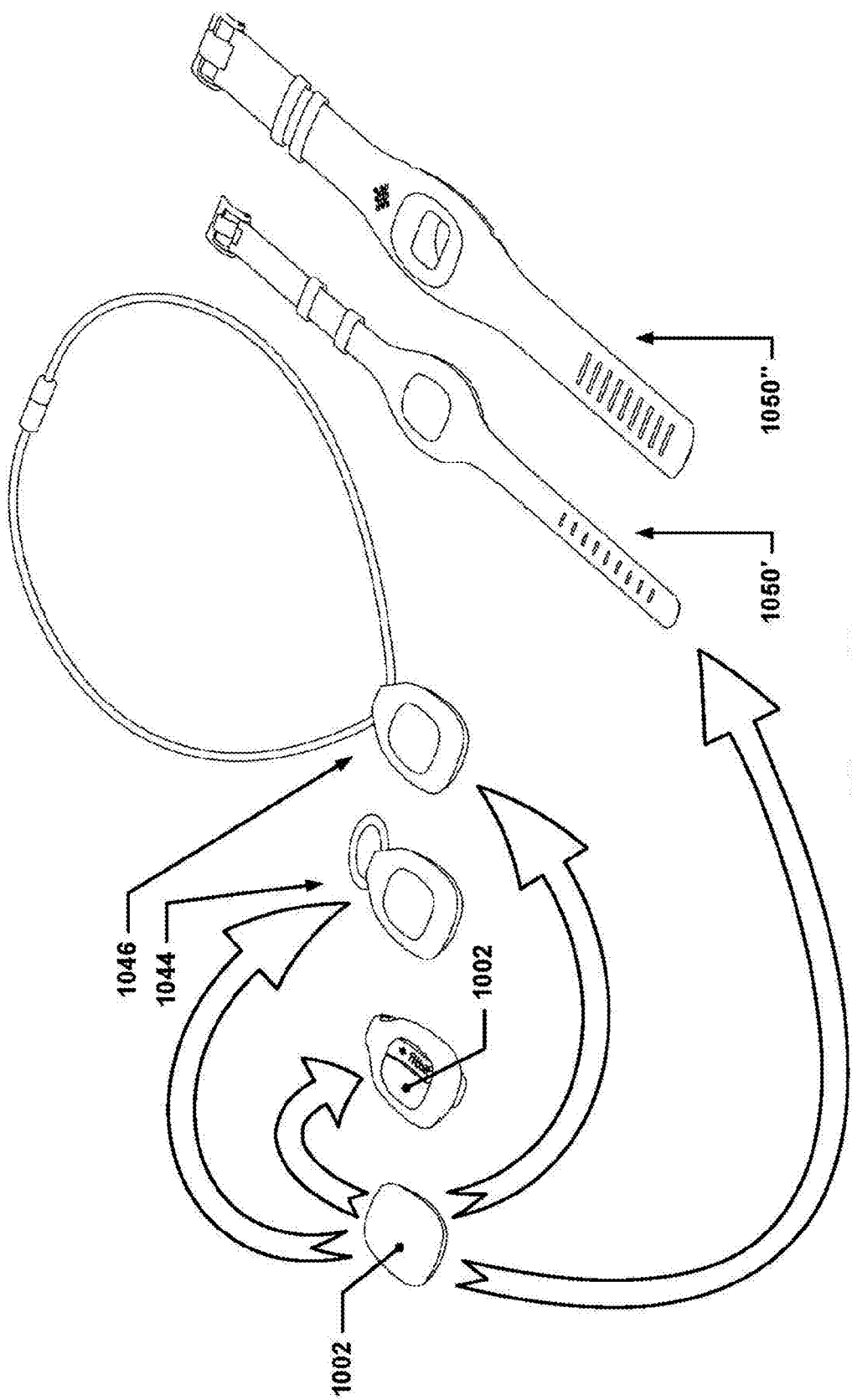
FIG. 10 depicts a variety of example cases which are compatible with a depicted example portable biometric monitoring device.

The present disclosure relates to wearable biometric monitoring devices (also referred to herein as "biometric tracking devices" or "biometric tracking modules") such as those, for example, illustrated in FIGS. 1-4C, and cases for housing biometric monitoring devices that feature mechanical straps, bands, clasps, clips and other attachments to enable wear (illustrated in FIGS. 5 through 14C). In several implementations, a set of protective, attachable and/or wearable cases (herein referred to simply as "cases") that enable a user to wear a single biometric monitoring device in multiple fashions or body locations may be provided. For example, in some implementations, a biometric monitoring device may be designed such that it may be inserted into, and removed from, a plurality of compatible cases. In other implementations, the biometric monitoring devices may be permanently or semi-permanently mounted into (or joined to) straps, clips, clasps, bands, or other attachments for wear, such as is shown, for example, in FIGS. 13 through TT. Generally speaking, the various individual elements of the various example cases and/or biometric tracking devices shown herein may also be combined with elements from other example cases and/or biometric tracking devices shown herein, e.g., a necklace or pendant case for a removable biometric monitoring device, such as is shown in FIG. 10, may also be provided for a permanently-mounted biometric monitoring device. Such combinations of elements are considered to be within the scope of this disclosure. Generally speaking, a biometric monitoring device or biometric tracking device combined with a case or some other means allowing it to be worn or easily carried by a person may be referred to herein as a "biometric monitoring system" or "biometric tracking system."

Figure 1:
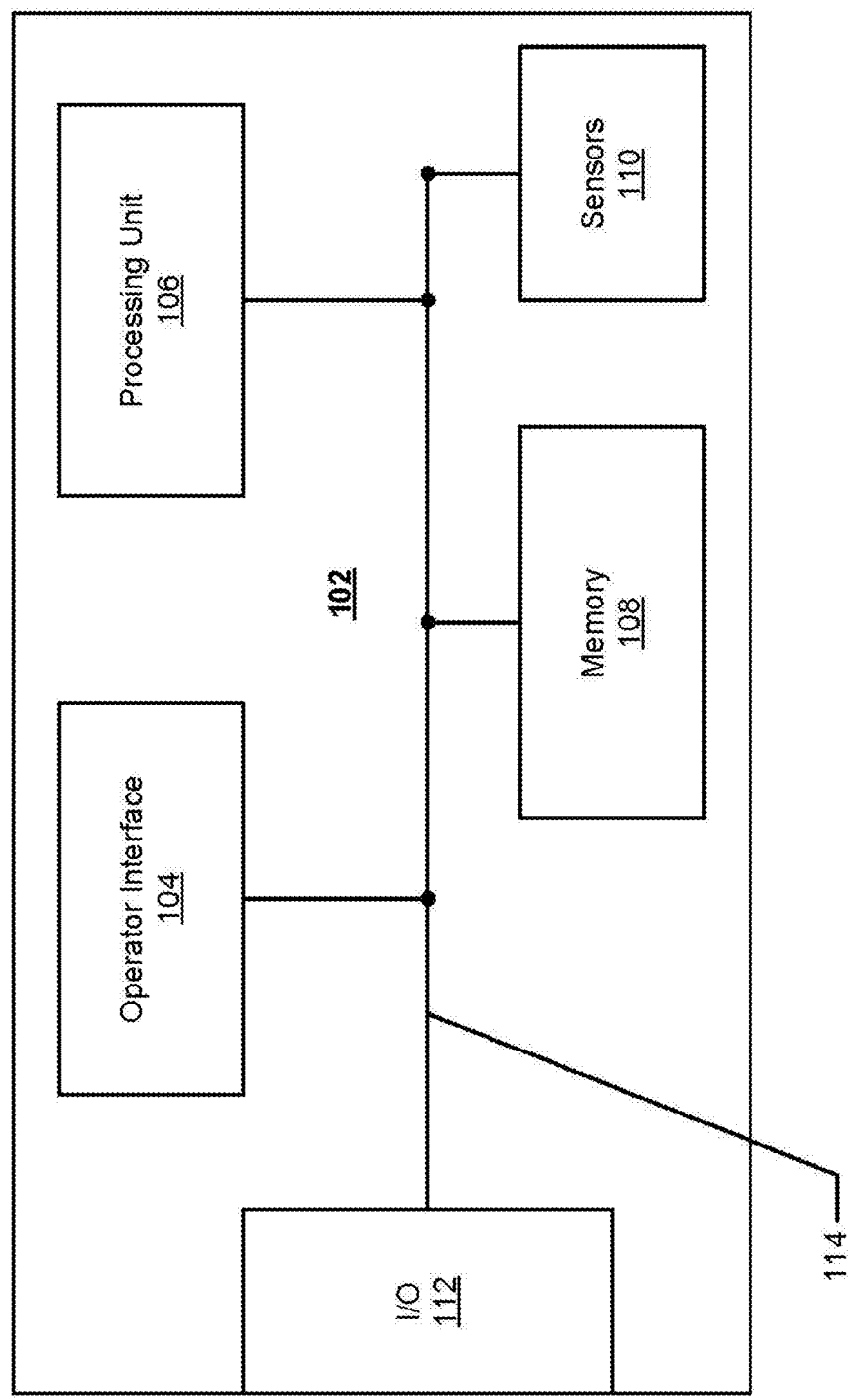
FIG. 1 depicts a generalized schematic of an example computing device that may be used to implement a portable biometric monitoring device or other device with which the various operations described herein may be executed.

FIG. 1 depicts a generalized schematic of an example portable biometric monitoring device or other device with which the various operations described herein may be executed. The portable biometric monitoring device 102 may include a processing unit 106 having one or more processors, a memory 108, an operator interface 104, one or more biometric sensors 110, and input/output 112. The processing unit 106, the memory 108, the operator interface 104, the one or more biometric sensors 110, and the input/output 112 may be communicatively connected via communications path(s) 114 (it is to be understood that some of these components may also be connected with one another indirectly).

The portable biometric monitoring device (also referred to herein as "the device") may collect one or more types of biometric data, e.g., data pertaining to physical characteristics of the human body (such as heartbeat, perspiration levels, etc.) and/or data relating to the physical interaction of that body with the environment (such as accelerometer readings, gyroscope readings, etc.), from the one or more biometric sensors 110 and/or external devices (such as an external heart rate monitor, e.g., a chest-strap heart rate monitor) and may then store such information for later use, e.g., for communication to another device via the I/O 112, e.g., a smartphone or to a server over a wide-area network such as the Internet. The processing unit 106 may also perform an analysis on the stored data and may initiate various actions depending on the analysis. For example, the processing unit 106 may determine that the data stored in the memory 108 indicates that a goal threshold has been reached and may then display content on a display of the portable biometric tracking device celebrating the achievement of the goal. The display may be part of the operator interface 104 (as may be a button or other control, not pictured, that may be used to control a functional aspect of the portable biometric monitoring device).

In general, biometric monitoring device may incorporate one or more types of user interfaces including but not limited to visual, auditory, touch/vibration, or combinations thereof. The biometric monitoring device may, for example, display the state of one or more of the data types available and/or being tracked by the biometric monitoring device through, for example, a graphical display or through the intensity and/or color of one or more LEDs. The user interface may also be used to display data from other devices or internet sources. The device may also provide haptic feedback through, for instance, the vibration of a motor or a change in texture or shape of the device. In some implementations, the biometric sensors themselves may be used as part of the user interface, e.g., accelerometer sensors may be used to detect when a person taps the housing of the biometric monitoring unit with a finger or other object and may then interpret such data as a user input for the purposes of controlling the biometric monitoring device. For example, double-tapping the housing of the biometric monitoring device may be recognized by the biometric monitoring device as a user input that will cause the display of the biometric monitoring device to turn on from an off state or that will cause the biometric monitoring device to transition between different monitoring states, e.g., from a state where the biometric monitoring device may interpret data according to rules established for an "active" person to a state where the biometric monitoring device may interpret data according to rules established for a "sleeping" person.

In another example, while the user is wearing the biometric monitoring device 102, the biometric monitoring device 102 may calculate and store a user's step count while the user is wearing the biometric monitoring device 102 and then subsequently transmit data representative of step count to the user's account on a web service like www.fitbit.com, to a mobile phone paired with the portable biometric monitoring unit, and/or to a standalone computer where the data may be stored, processed, and visualized by the user. Indeed, the device may measure, calculate, or use a plurality of other physiological metrics in addition to, or in place of, the user's step count. These include, but are not limited to, caloric energy expenditure, floors climbed or descended, heart rate, heart rate variability, heart rate recovery, location and/or heading (e.g., through GPS), elevation, ambulatory speed and/or distance traveled, swimming lap count, bicycle distance and/or speed, blood pressure, blood glucose, skin conduction, skin and/or body temperature, electromyography data, electroencephalographic data, weight, body fat, and respiration rate. Some of this data may be provided to the biometric monitoring device from an external source, e.g., the user may input their height, weight, and stride in a user profile on a fitness-tracking website and such information may then be communicated to the biometric tracking device and used to evaluate, in tandem with data measured by the biometric sensors 110, the distance traveled or calories burned of the user. The device may also measure or calculate metrics related to the environment around the user such as barometric pressure, weather conditions, light exposure, noise exposure, and magnetic field.

As mentioned previously, collected data from the biometric monitoring device may be communicated to external devices through the communications interface. The communications interface may include wireless communication functionality so that when the biometric monitoring device comes within range of a wireless base station or access point, the stored data automatically uploads to an Internet-viewable source such as a website, e.g., www.fitbit.com. The wireless communications functionality may be provided using one or more communications technologies known in the art, e.g., Bluetooth, RFID, Near-Field Communications (NFC), Zigbee, Ant, optical data transmission, etc. The biometric monitoring device may also contain wired communication capability, e.g., USB.

Other implementations regarding the use of short range wireless communication are described in U.S. patent application Ser. No. 13/785,904, titled "Near Field Communication System, and Method of Operating Same" filed Mar. 5, 2013 which is hereby incorporated herein by reference in its entirety.

It is to be understood that FIG. 1 illustrates a generalized implementation of a biometric monitoring device 102 that may be used to implement a portable biometric monitoring device or other device in which the various operations described herein may be executed. It is to be understood that in some implementations, the functionality represented in FIG. 1 may be provided in a distributed manner between, for example, an external sensor device and communication device, e.g., a chest-strap heart rate sensor that may communicate with a biometric monitoring device.

Moreover, it is to be understood that in addition to storing program code for execution by the processing unit to effect the various methods and techniques of the implementations described herein, the memory 108 may also store configuration data or other information used during the execution of various programs or instruction sets or used to configure the biometric monitoring device. It is to be further understood that the processing unit may be implemented by a general or special purpose processor (or set of processing cores) and thus may execute sequences of programmed instructions to effectuate the various operations associated with sensor device syncing, as well as interaction with a user, system operator or other system components. In some implementations, the processing unit may be an application-specific integrated circuit.

Though not shown, numerous other functional blocks may be provided as part of the biometric monitoring device 102 according to other functions it may be required to perform, e.g., environmental sensing functionality, etc. Other functional blocks may provide wireless telephony operations with respect to a smartphone and/or wireless network access to a mobile computing device, e.g., a smartphone, tablet computer, laptop computer, etc. The functional blocks of the biometric tracking device 102 are depicted as being coupled by the communication path 114 which may include any number of shared or dedicated buses or signaling links. More generally, however, the functional blocks shown may be interconnected using a variety of different architectures and may be implemented using a variety of different underlying technologies and architectures. With regard to the memory architecture, for example, multiple different classes of storage may be provided within the memory 108 to store different classes of data. For example, the memory 108 may include non-volatile storage media such as fixed or removable magnetic, optical, or semiconductor-based media to store executable code and related data and/or volatile storage media such as static or dynamic RAM to store more transient information and other variable data.

The various methods and techniques disclosed herein may be implemented through execution of one or more a sequences of instructions, e.g., software programs, by the processing unit 106 or by a custom-built hardware ASIC (application-specific integrated circuit) or programmed into a programmable hardware device such as an FPGA (field-programmable gate array), or any combination thereof within or external to the processing unit 106.

Further implementations and implementations of portable biometric monitoring devices can be found in U.S. patent application Ser. No. 13/156,304, titled "Portable Biometric Monitoring Devices and Methods of Operating Same" filed Jun. 8, 2011, which is hereby incorporated herein by reference in its entirety.

In some implementations, the biometric monitoring device may include computer-executable instructions for controlling one or more processors of the biometric monitoring device to obtain biometric data from one or more biometric sensors. The instructions may also control the one or more processors to receive a request, e.g., an input from a button or touch interface on the biometric monitoring device, a particular pattern of biometric sensor data (e.g., a double-tap reading), etc., to display an aspect of the obtained biometric data on a display of the biometric monitoring device. The aspect may be a numerical quantity, a graphic, or simply an indicator (a goal progress indicator, for example). In some implementations, the display may be an illuminable display so as to be visible when displaying data but otherwise invisible to a casual observer. The instructions may also cause the one or more processors to cause the display to turn on from an off state in order to display the aspect of the biometric data.

Figure 2B:
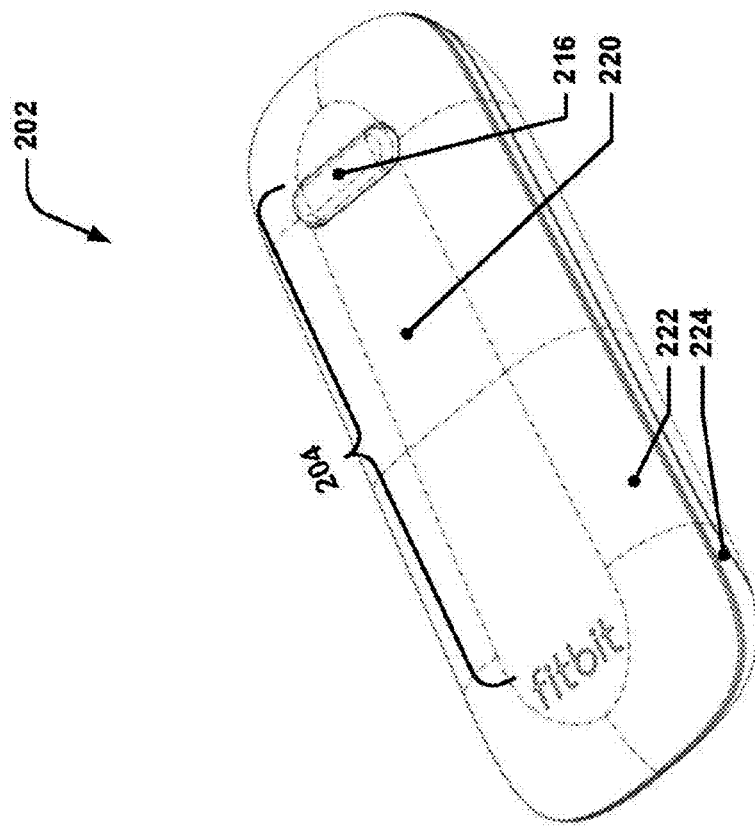
FIG. 2B depicts an isometric view of the example of the portable biometric monitoring device of FIG. 2A.
Figure 2A:
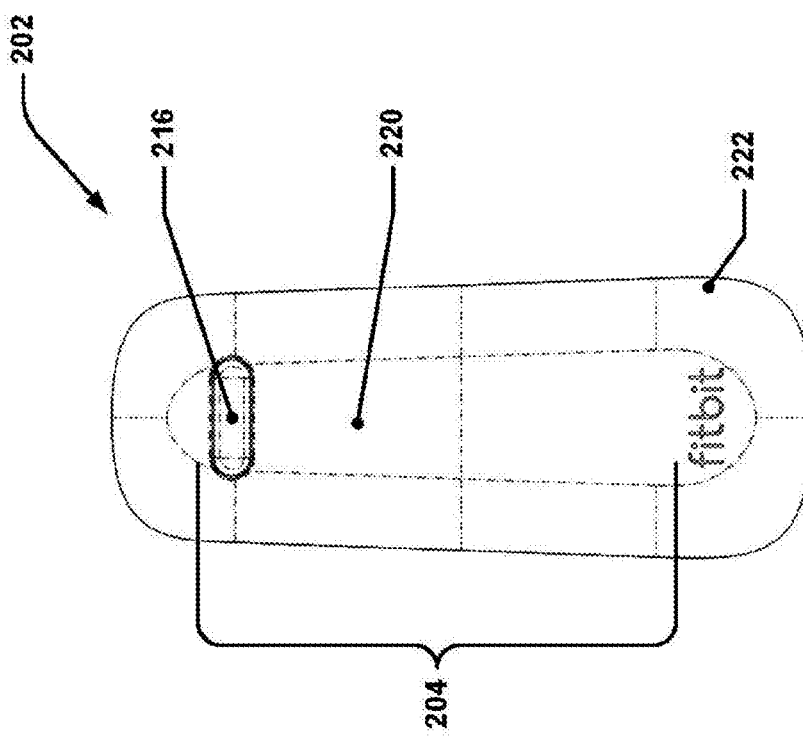
FIG. 2A depicts a plan view of an example of a portable biometric monitoring device having a button and a dead face display.
Figure 2C:
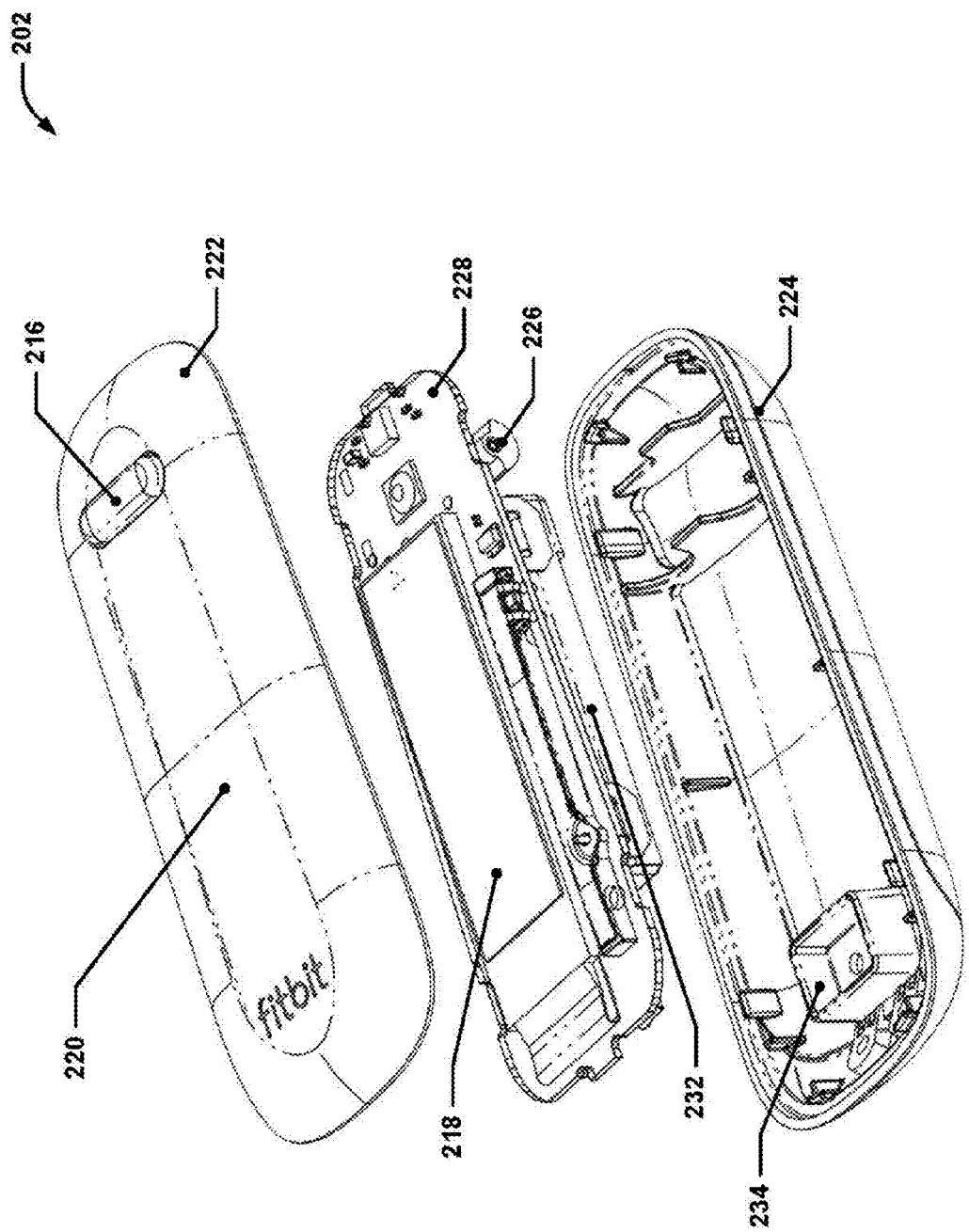
FIG. 2C depicts an exploded view of the example of the portable biometric monitoring device of FIG. 2A.

FIG. 2A depicts a plan view of an example of a portable biometric monitoring device having a button and a dead face display. FIG. 2B depicts an isometric view of the example of the portable biometric monitoring device of FIG. 2A. FIG. 2C depicts an exploded view of the example of the portable biometric monitoring device of FIG. 2A.

The depicted biometric monitoring device in FIGS. 2 through CC is similar to the Fitbit One™, and may be similarly sized, e.g., approximately 1.9" in length, 0.75" wide, and 0.375" thick. A button 216 may be provided to allow a user to interact with the biometric monitoring device 202; the button 202 may be used, for example, to cause display 218 to turn on from an off state or to advance through a plurality of data views. The button 202 and the display 218 may be part of an operator interface 204. A portion of the operator interface 204, e.g., the display 218, may be obscured from the user's view by a front housing 222. The front housing 222 may be made or partially made from a partially translucent or transparent material that permits the display to be seen through the front housing, allowing the display 218 to be fully contained within the biometric monitoring device 202. In some implementations, the front housing 222 may be made from a material causes the display 218 to only be transiently visible, i.e., only easily visible to a user when the display is displaying content. Examples of such materials include, but are not limited to, smoked translucent plastics, frosted translucent plastics, and reflective translucent or transparent materials. The display 218 in such implementations may be a backlit or LED display to allow displayed content to shine through the front housing 222. Such materials may have an opacity or reflectivity that substantially prevents a person from discerning any significant detail of objects located on the other side of a surface made of such material but that permits light emitted from such objects to pass through the surface to reach the observer. For example, such materials may have a light transmittance of between about 15% and 50%, 10% and 60%, 5% and 70%, or combinations thereof.

The biometric monitoring device 202 may include a PCB 228, a battery 232, and various other components that are housed within the front housing 222 and the back housing 224. Among these other components may be one or more biometric sensors selected from a variety of different types of biometric sensors, e.g., accelerometers, gyroscopes, etc. One type of biometric sensor that may be included is a barometric altimeter. In order to allow such a barometric altimeter to measure ambient atmospheric conditions while preventing liquid, e.g., rain or sweat, from entering and damaging electronics in the interior of a portable biometric monitoring device, a gas permeable, liquid-impermeable (or liquid-resistant) membrane such as a Gore™ vent may be used. Such a membrane may be placed over a hole in the device body, allowing the pressure from the exterior of the case to equalize with the pressure sensor on the interior.

Alternatively, or in addition, to the use of a Gore™ vent, a gasket 234 located in the interior of the biometric monitoring device may be used. In one implementation, the barometric altimeter/pressure sensor may be mounted to the PCB 228. A thin, flexible water impermeable membrane may cover the barometric altimeter/pressure sensor in a manner that allows the barometric altimeter/pressure sensor to still detect the local pressure on the opposite side of the membrane while preventing any water or moisture that may be present from crossing over the membrane. The membrane may, for example, be adhered to the PCB 228. Other features of the biometric monitoring device, e.g., altimeter gasket 234, may seal against the membrane and front housing 222 or the back housing 224 when the biometric monitoring device is fully assembled to create a water-tight pressure measurement chamber that is sealed off from the electronics of the biometric monitoring device but that nonetheless permits pressure measurements of the conditions within the pressure measurement chamber by the barometric altimeter/pressure sensor through the membrane. Such a feature may prevent water or other liquids from entering the biometric monitoring device except within the pressure measurement volume bounded by the altimeter gasket 234, membrane, and interior surface of the front housing 222 or the back housing 224 (or other housing equivalent). Such a segregated pressure measurement volume may also prevent pressure changes from the interior of the biometric monitoring device from being detected by the barometric altimeter/pressure sensor. For example, if deformation of the biometric monitoring device case causes a pressure change within the housing, isolating the pressure sensor from the rest of the biometric monitoring device housing may eliminate or reduce the pressure change detected by the barometric altimeter/pressure sensor due to such deformation.

Figure 3:
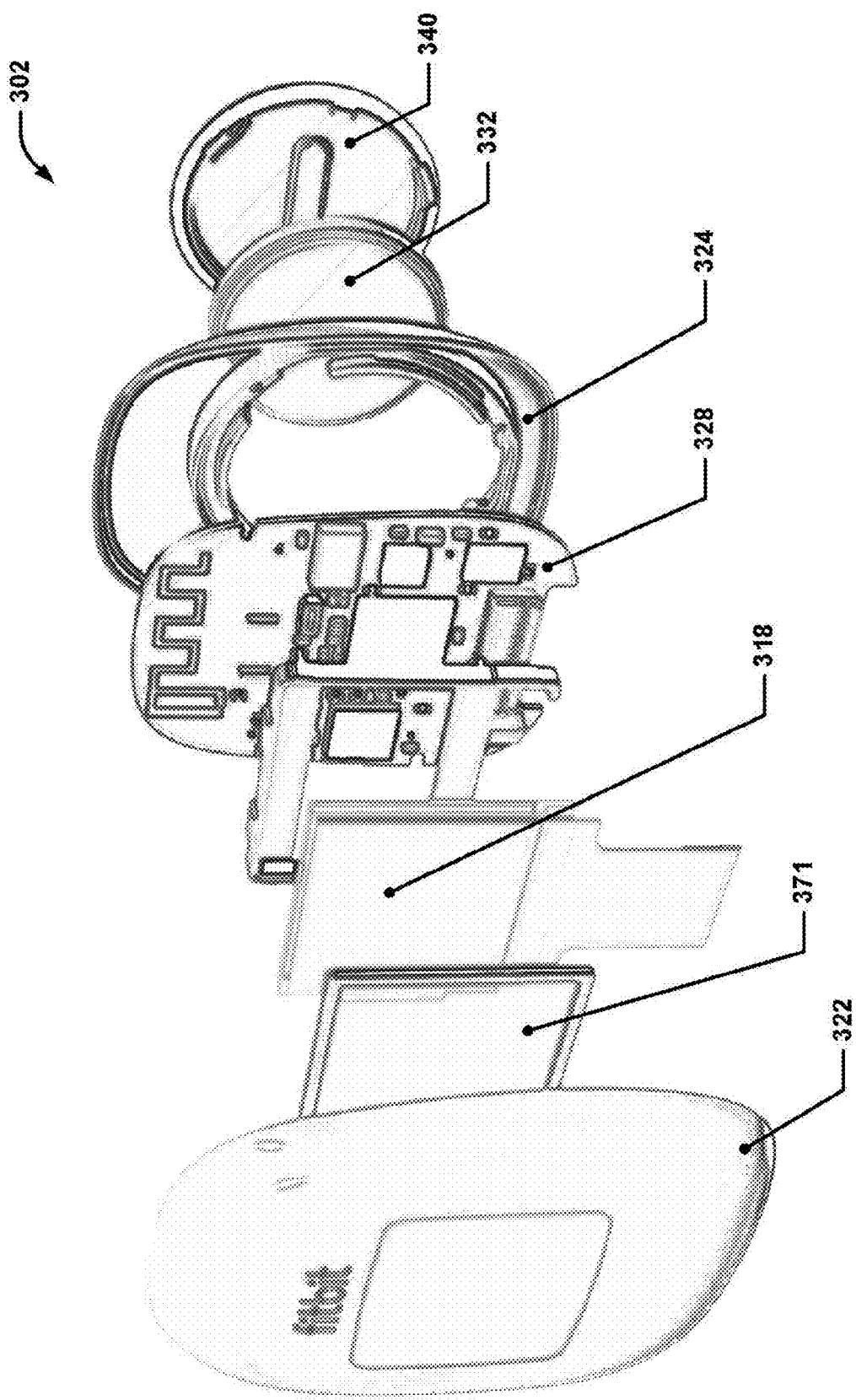
FIG. 3 depicts an exploded view of another example of a portable biometric monitoring device.

FIG. 3 depicts an exploded view of another example of a portable biometric monitoring device. In FIG. 3, a biometric monitoring device 302 may be provided within an enclosure formed between a front housing 322 and a back housing 324. A display 318 may be visible through a window 371 in the front housing 322. A printed circuit board (PCB) 328 may house various other electronic components, e.g., one or more processors, one or more biometric sensors, one or more communications interfaces, etc., that may be used to provide biometric monitoring functionality to the portable biometric monitoring device 302. Power for the biometric monitoring device 302 may be provided from, for example, battery 332, which may be a replaceable battery held in place behind a battery cover 340. While FIG. 3 depicts a variant that is designed to use a disposable button cell battery, other variants may utilize a rechargeable battery (e.g., such as the version shown in FIGS. 2A through 2C).

The biometric monitoring device of FIG. 3 is similar to the Fitbit Zip™, which has dimensions of approximately 1.1" by 1.4" by 0.375" and is powered by a 3V coin battery.

Figure 4A:
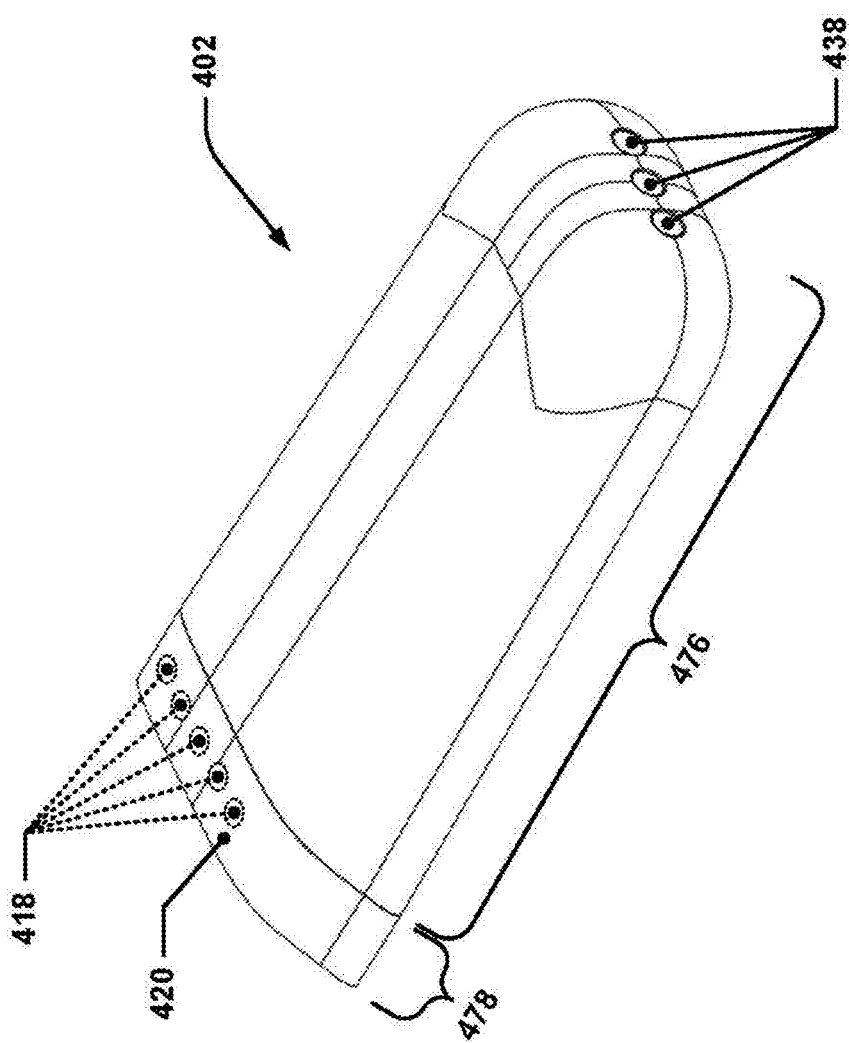
FIG. 4A depicts another example of a portable biometric monitoring device.
Figure 4B:
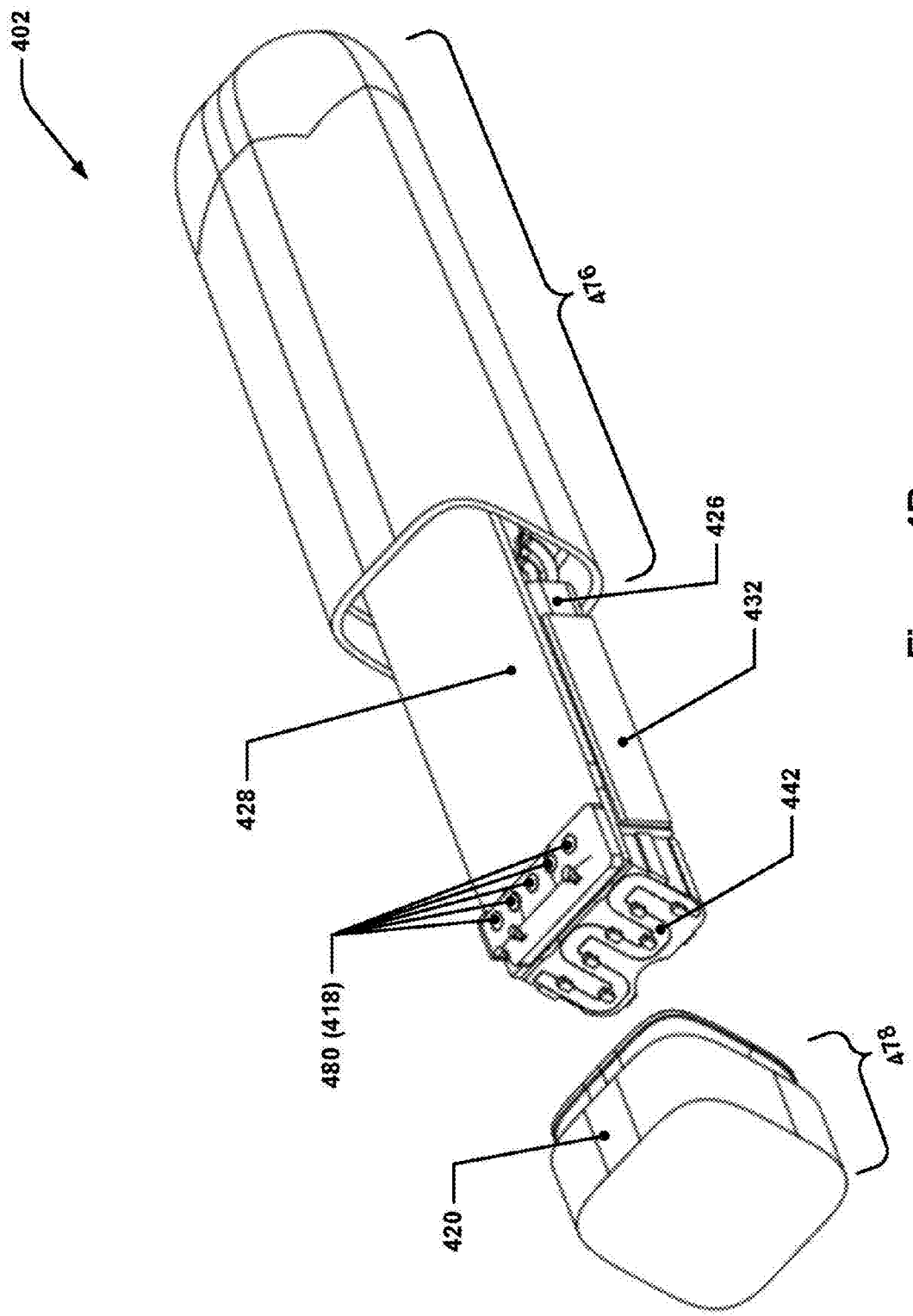
FIG. 4B depicts a partially-exploded view of the example of the portable biometric monitoring device of FIG. 4A.
Figure 4C:
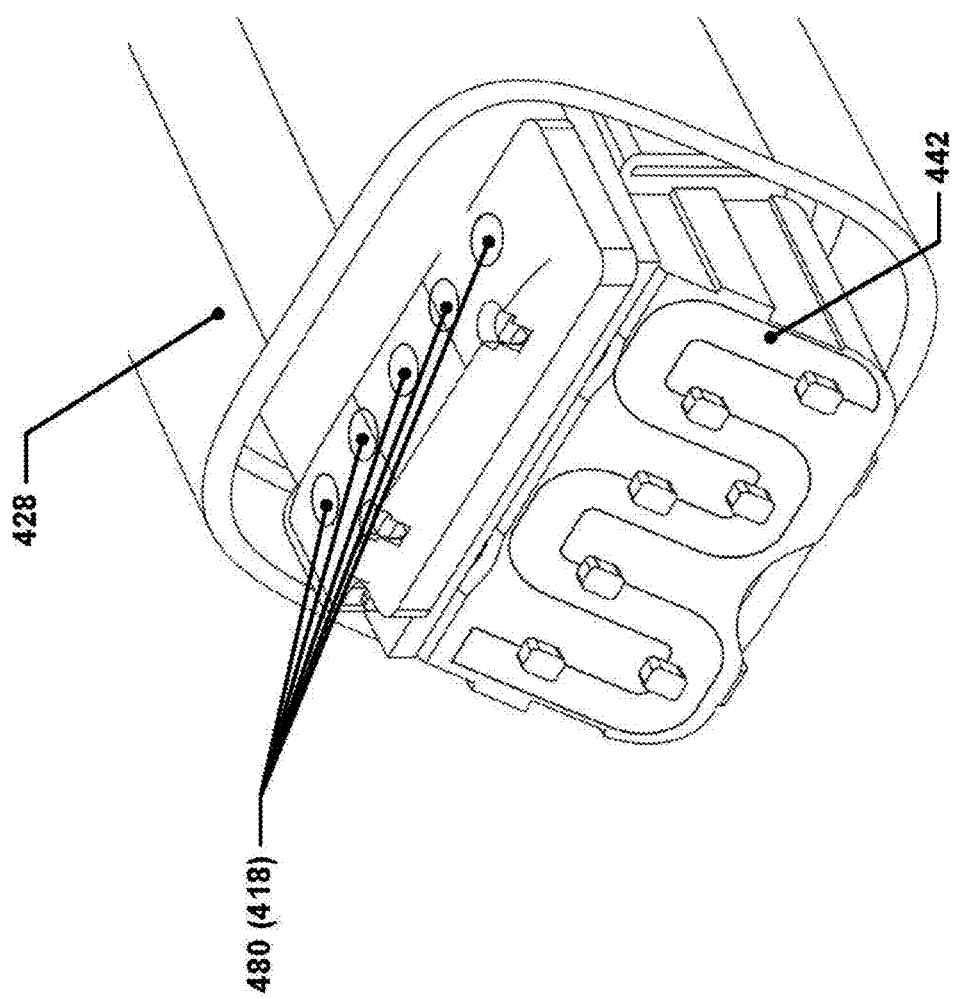
FIG. 4C depicts a detailed view of light pipes used to direct and shape the light emitted from one or more LEDS in the example of the portable biometric monitoring device of FIG. 4A, as well as an antenna located on the electronics package seen in FIG. 4B.

FIG. 4A depicts another example of a portable biometric monitoring device. FIG. 4B depicts a partially-exploded view of the example of the portable biometric monitoring device of FIG. 4A. FIG. 4C depicts a detailed view of light pipes used to direct and shape the light emitted from one or more LEDS in the example of the portable biometric monitoring device of FIG. 4A, as well as an antenna located on the electronics package seen in FIG. 4B.

In FIG. 4A, a biometric monitoring device 402 is depicted. In the biometric monitoring device 402 shown, the front housing/back housing arrangements discussing with respect to other devices shown in this disclosure have been replaced with a single-piece housing 476. The electronics of the biometric monitoring device may be located on PCB 428, which may be slid into the housing 276 and held in place by the cap 278.

In the implementation shown, e.g., in FIGS. 4B and 4C, the display 418 may be provided by one or more LED indicators (or other light sources) instead of a pixelated display unit. In the particular implementation shown, there are five LED indicators arranged in a line. In some implementations, light pipes 480 (or other light guiding/masking features) may be interposed between the display 418 and, for example, the cap 478 or the housing 476. Also visible in FIGS. 4B and 4C is antenna 442, which may be part of an input/output system, e.g., communications interface, of the biometric monitoring device. The antenna 442 may be used to send and receive signals from, for example, a paired smartphone or other portable electronic device, another biometric monitoring device (for example, a biometric monitoring device worn by a jogging partner), or a charging/docketing station. A battery 432 and a vibramotor 426 may also be included within the housing 476, and may be mounted to the PCB 428 to allow the entire electronics package of the biometric monitoring device 402 to be slid inside the housing 476 as a unit.

The biometric monitoring device 402 shown in FIGS. 4A through 4C is similar to a Fitbit Flex device, which is approximately 1.3" in length, 0.5" wide, and 0.25" thick.

Figure 5:
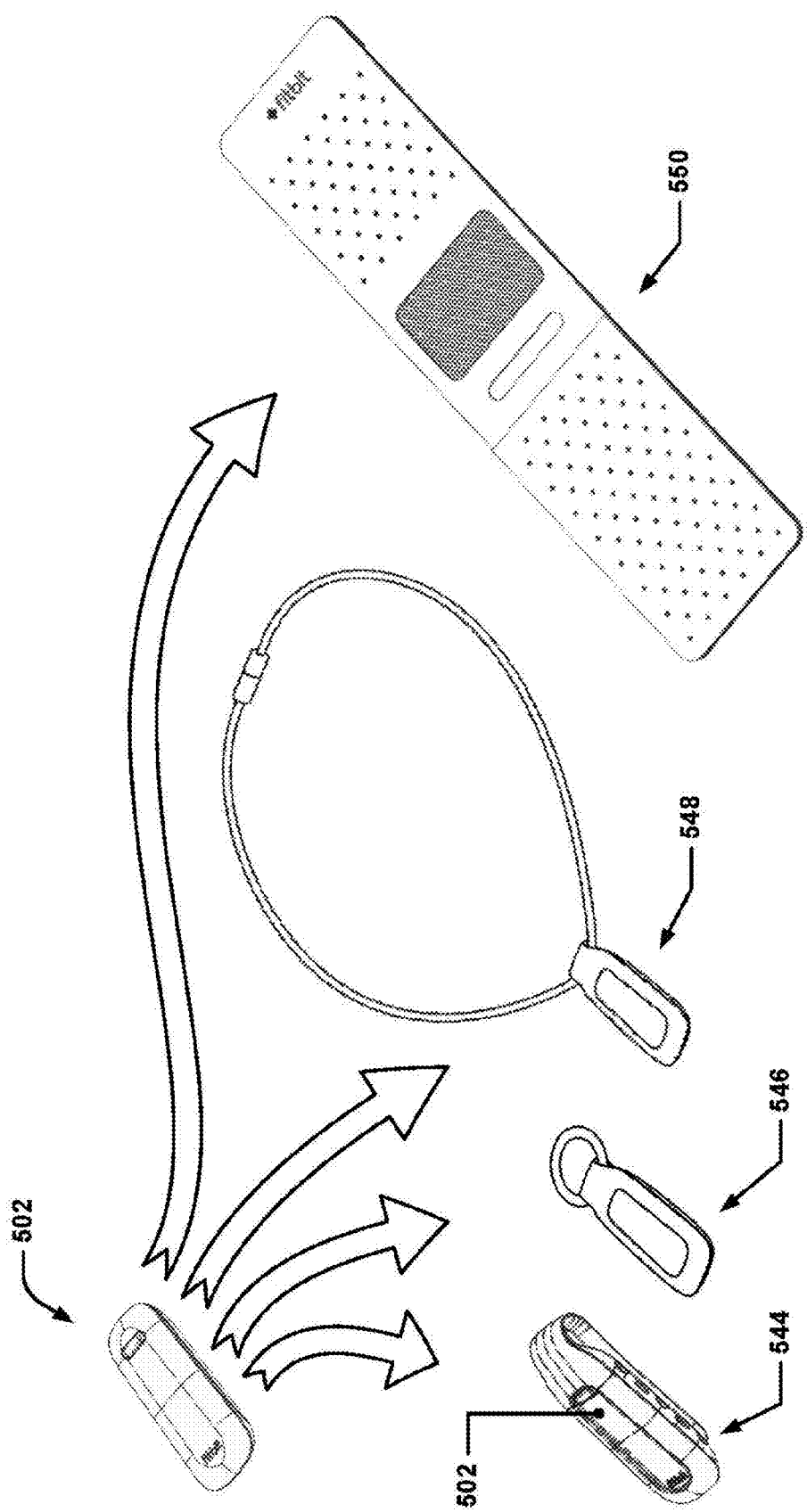
FIG. 5 depicts a number of example cases that may be used with the depicted example portable biometric monitoring device.
Figure 6:
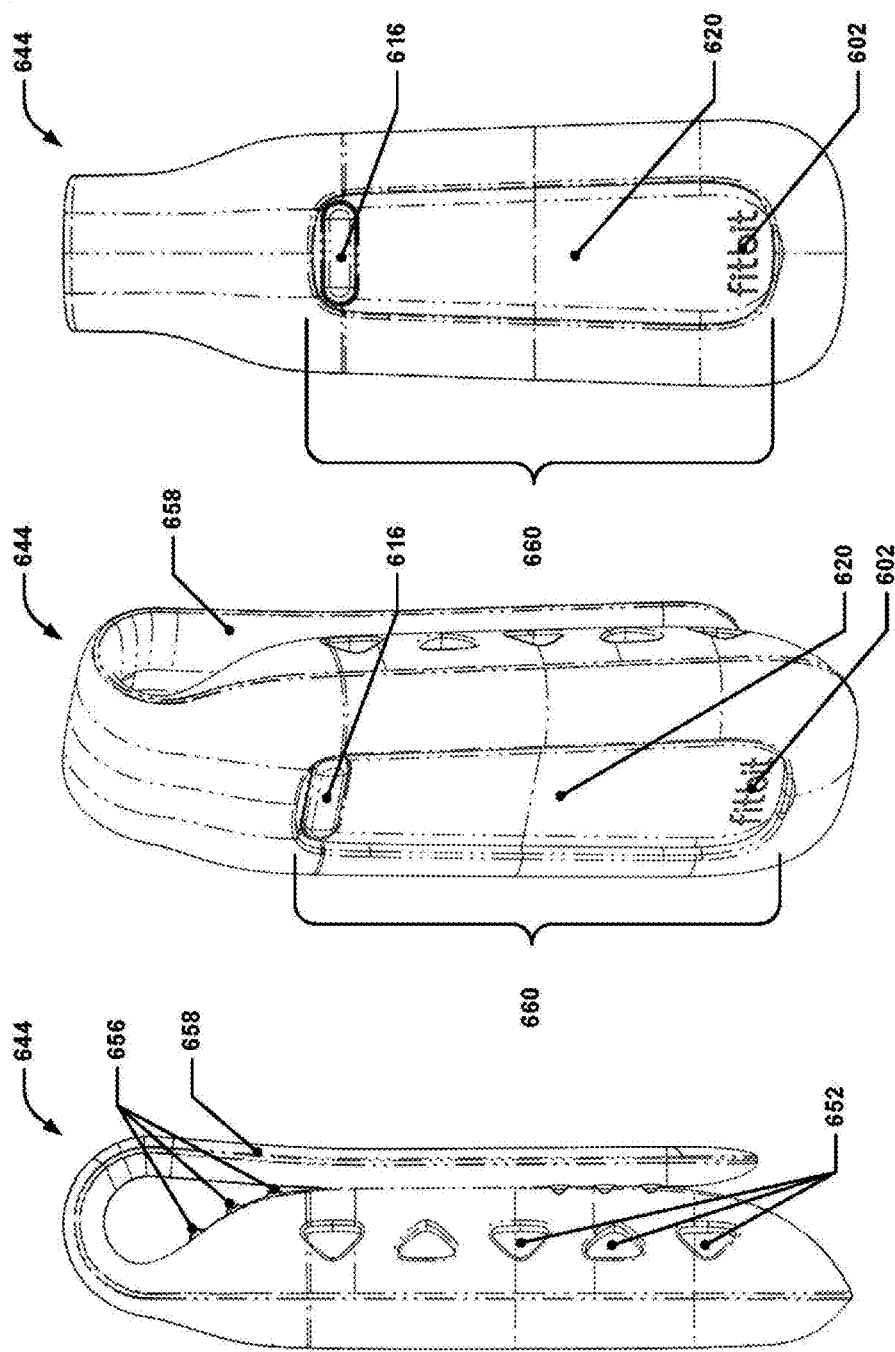

FIG. 5 depicts a number of example cases that may be used with the depicted example portable biometric monitoring device. In FIG. 5, a biometric monitoring device 502, which is similar to the biometric monitoring device 202, is shown. A suite of different wearable accessories may be provided that allow the biometric monitoring device 502 to be worn in a variety of ways. The biometric monitoring device 502 is fully insertable into each of the depicted wearable accessories, providing a secure way to secure the biometric monitoring device 502 to a wearer's person.

Biometric monitoring devices and cases such as those discussed above may be designed to allow the biometric monitoring device to be easily attached/inserted and removed from any of a suite of different wearable attachments. The biometric monitoring device may be attached to all of the cases using the same attachment method or through different attachment methods for one or more different cases. Additionally, a combination of attachment methods may be used to create a more secure connection of the biometric monitoring device to the case.

In one example of an additional attachment technique, the biometric monitoring device may be secured to the case though the use of a permanent magnet or electromagnet. There may be a magnet in the device and the case may contain a ferrous metal. Alternatively, the case may contain a permanent magnet while the device or device body contains ferrous metal. In another example, the case and the device may both contain magnets. In such a case, the magnets may be installed to force the device to be secured to the case with a specific orientation due to the force created by the interaction of the two magnets. Permanent magnets or electromagnets may be used in place of or in addition to mechanical retention techniques.

A clip case 544 may allow the biometric monitoring device 502 to be clipped to a belt, pocket, or other portion of a wearer's clothing. If the biometric monitoring device 502 is inserted into a keychain case 546, the keychain case 546/biometric monitoring device 502 may be used to carry the wearer's keys, or may be securely clipped to a belt loop, zipper pull, or other feature of the wearer's clothing. A necklace case 548 may allow the biometric monitoring device 502 to be worn around the wearer's neck as a pendant. In some implementations, the pendant of the necklace case 548 and the fob of the keychain case 546 may be provided by the same structure, i.e., the "ring" of the keychain may be exchanged for the "chain" or "lanyard" of the necklace without removing the biometric monitoring device 502 from the pendant/fob structure.

Each of the clip case 544, the keychain case 546, and the necklace case 548 may be constructed out of one or more materials including but not limited to metals and/or flexible/compliant viscoelastic materials. Flexible compliant viscoelastic materials (herein referred to as viscoelastics) may include, but are not limited to thermoset elastomers (rubber), thermoplastic elastomers (TPE), thermoplastic vulcanizates, silicones, and/or polyurethanes (including thermoplastic polyurethanes (TPU)). For example, the bulk of such cases may be made from a viscoelastic material and may be formed around a metal or other more rigid material that forms a semi-rigid structural backbone or that may be used to provide additional stiffness for components that require it, e.g., for the clip on a clip case. Generally speaking, flexible materials suitable for manufacturing a clip case, a keychain case, a necklace case, or a wristband case may include materials having elastic moduli of 15 to 60 MPa, 3.6 to 120 MPa, 69 to 690 MPa, 1 to 50 MPa, or combinations of such elastic moduli.

In addition to the viscoelastic cases represented by the clip case 544, the keychain case 546, and the necklace case 548, another type of case that is envisioned is a textile-based wristband case 550. Such a textile-based wristband case 550 is also discussed in further detail later in this disclosure.

Returning to the clip case 544, the keychain case 546, and the necklace case 548, certain observations may be made. The biometric monitoring device 502 may have a generally smooth and rounded exterior that permits it to be easily slid into a silicone or other flexible viscoelastic case, e.g., such as the clip case 544, the keychain case 546, and/or the necklace case 548. Each such case may be designed and constructed so as to balance the degree of retention of the device with the ability of a wearer to easily remove and reinsert the biometric monitoring device 502 into the case. The biometric monitoring device may be inserted into an opening in the viscoelastic material of the case that is smaller than one or more dimensions of the device, e.g., smaller than a maximum dimension of the biometric monitoring device (as measured along a diagonal or along one of three mutually-orthogonal axes aligned with standard top/front/side views of the biometric monitoring device 502). By stretching the viscoelastic opening, the opening can be expanded enough to allow the biometric monitoring device 502 to be inserted into the case. The elasticity of the viscoelastic causes it to return to its original size, preventing the device from accidentally falling out of the case.

FIGS. 6A, 6B, and 6C depict various views of an example of a portable biometric monitoring device case having a clip. As shown in FIGS. 6A, 6B, and 6C, a biometric monitoring device 602 may be inserted into a clip case 644 through opening 660. A receptacle or cavity within the clip case 644 may be accessible via the opening and may be sized to receive the biometric monitoring device such that an interior surface of the receptacle is in contact with the biometric monitoring device 602 when the biometric monitoring device 602 is fully inserted into the receptacle. It is to be understood that, as used herein, when the term "contact" is used in the context of two surfaces that contact one another within a specified area or region, it is to be understood that such reference indicates that such surfaces are in substantial contact with one another within that area or region. For example, due to surface roughness or localized texturing of one or both surfaces, true contact between the two surfaces may actually be limited to a small portion of the specified area or region, e.g., those portions where one or both surfaces have elevation peaks. Such true contact, however, may occur in a distributed manner across the specified area or region, and such surfaces may thus be described as being "in contact" with one another within the specified area or region.

Figure 7:
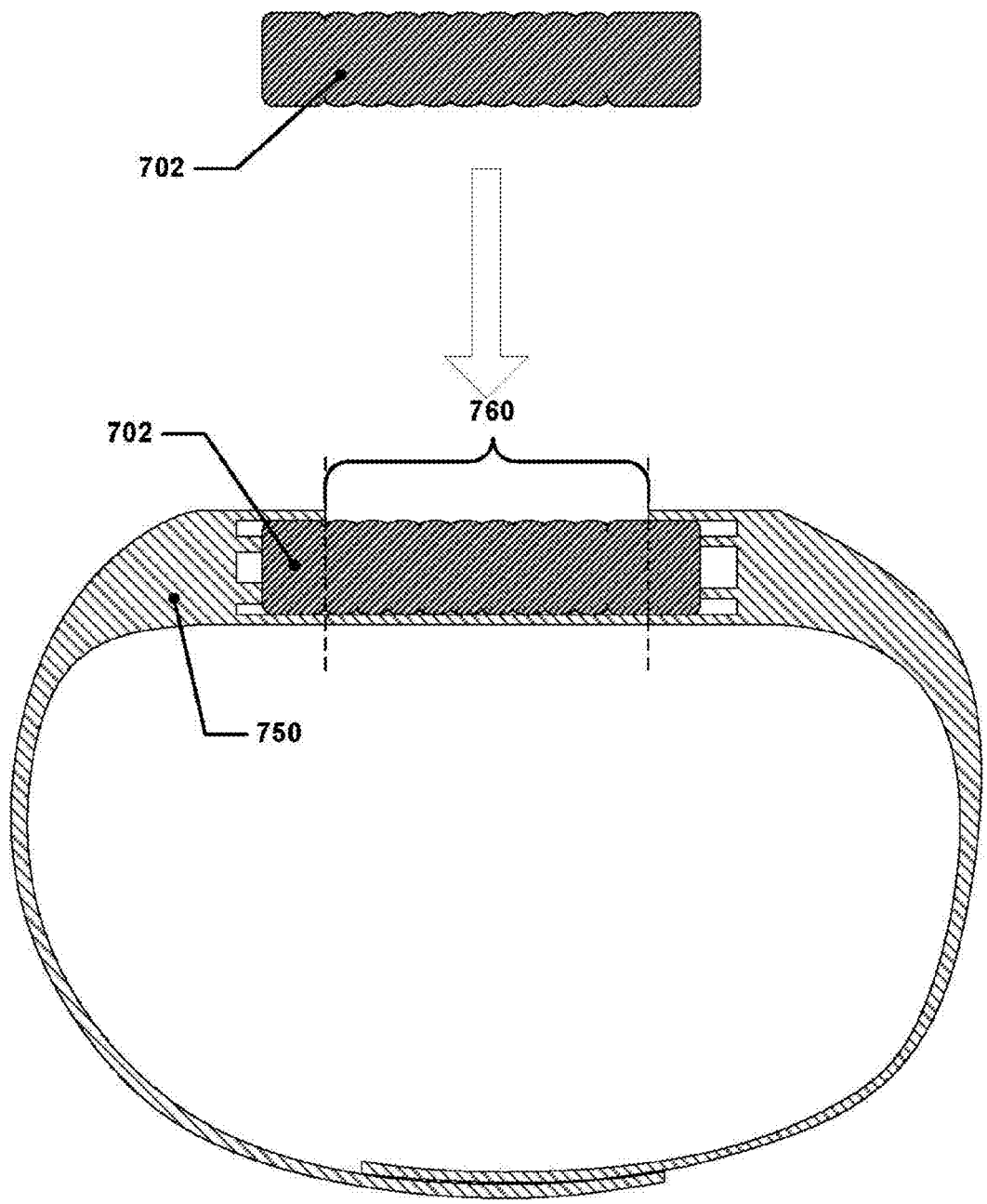
FIG. 7 depicts a wristband case made from a viscoelastic material.

For example, FIG. 7 depicts a wristband case made from a viscoelastic material, similar to the wristband cases discussed with respect to FIGS. 11A through 11F later in this disclosure. In the depicted example, a biometric monitoring device 702 inserted into the wristband case 750 via an opening 760 may have a textured, e.g., ribbed, exterior surface. While the interstices between each rib may not be in true contact with the interior surface of the receptacle within which the biometric monitoring device 702 is inserted, the peaks of each rib may be in actual contact with the interior surface. Thus, within the region of the interior surface of the receptacle between the two dashed lines, it is to be understood that the interior surface is "in contact" with the exterior surface of the biometric monitoring device 702 despite the non-contact between the rib interstices and the interior surface. Similarly, if the interior surface has embossed or raised lettering, e.g., a part number, that resulted in some small gaps between the interior surface and a contacting exterior surface in the vicinity of the lettering, such surfaces would still be "in contact" with one another over the lettering area.

In some implementations, the opening in the viscoelastic material of the case may also act as a window to the display of the device (as seen in FIG. 6A for example). In other implementations, there may be other openings in the case which allow the user to see visual indicators and/or enable sensors on the device to function properly. For example, a window or vent on the case could be used to allow a pressure sensor to accurately determine the atmospheric pressure even when the biometric monitoring device is encased within the case. In another example, a window in the case may allow an optical heart rate sensor to have a clear optical pathway to the skin of the user.

In some implementations, one or more channels, tubes, and/or holes may connect the pressure sensor of the device to the exterior of the case as seen with ventilation holes 652 in FIG. 6A. The ventilation holes 652 may be functional (when coinciding with a pressure sensor location) or may be decorative. The ventilation holes 652, however, may be sized to be considerably smaller than the opening 660 so as to prevent the biometric monitoring device 602 from slipping out of the clip case 644 via the ventilation holes 652.

In another implementation, the case may be designed to transfer pressure from the exterior of the case to a pressure sensor in the device through the use of a pressure-transmissive membrane or material. In another example, a window in the case could be used to allow optical light sources and sensors to interact with the environment outside of the case effectively. In yet another implementation, the viscoelastic of the case may be transparent either in one area, multiple areas, or everywhere so as to allow visual indicators or displays to be seen through the case and/or to give optical sensors an optical path to the exterior of the case. Case transparency may be achieved by making or more areas of the case thin (for example by molding). Thin case areas made out of semitransparent material (e.g. viscoelastic) can be transparent enough for visual indicators such as displays and LEDs to be seen and light sensors to be able to measure light from the exterior of the case, but may otherwise mask the appearance of the components behind the thin sections. Thus, the case may present an unbroken surface in the area over the display, but the display may still be visible through the unbroken surface when displaying content. When the display is off, then the case may present a largely featureless surface over the display.

In the pictured implementation, the opening 660 may also serve as a window through which a display 618 of the biometric monitoring device 602 may be observed, as well as a window through which a button 616 of the biometric monitoring device 602 may be accessed.

The clip case 644 may also have a retention clip 658 that is configured to press against a side of the clip case 644 opposite the opening 660. The clip case 644 may be worn in any location where the clip can grasp a portion of what the user is wearing, where clothing or other material may be slid in between the retention clip 658 and the remainder of the clip case 644. These locations may include, but are not limited to, clipping the case to the user's pocket, belt, belt loop, waistband, shirt sleeve, shirt collar, shoe, shoelaces, hat, bra, tie, sock, underwear, coin pocket, or other articles of clothing, as well as to accessories such as a purse, backpack, belt pack, fanny pack, goggles, swim cap, glasses, sunglasses, necklace, pendant, pin, hair accessory, or earring. The retention clip 658 may be made out of a material such as polyurethane molded in such a form so as to accept a piece of spring steel that increases the spring force exerted by the retention clip 658 on the remainder of the clip case 644 such that the friction exerted on any material inserted between the retention clip 658 and the clip case 644 is higher than may be attained were the spring steel to be omitted. This may promote retention of the clip case 644 on the wearer's person. In other implementations, the retention clip may include a bare metal retention clip 658 (without being embedded within a polyurethane or other material), or may include a material other than polyurethane that surrounds a metal retention clip. In some implementations, the retention clip may not include any spring steel (or other metal) and may be made from plastic, e.g., molded polyurethane. In some implementations, the clip case 644 may also include one or more protrusions 656 or nubs on the side of the clip case 644 that faces the retention clip 658. The protrusions 656 may act to provide the retention clip 658 and clip case 644 with additional grip when attached to a wearer's clothing.

FIG. 8 depicts two different example cases for a depicted example portable biometric monitoring device. In FIG. 8, a biometric monitoring device 802 is shown, along with a keychain case 846 and a necklace case 848. In some implementations, the keychain case 846 may, as discussed previously, share the same fob/pendant as the necklace case 848. In some further implementations, the keychain case 846 and the necklace case 848 may use a clip case 844 as the fob and/or the pendant. The keyring used for a keychain case 846 may be a split-ring, a lift-open/snap-shut ring, or some other type of ring. Similarly, the lanyard, chain, string, or cord used for the necklace case 848 may be split or otherwise removable (the cord may be continuous, for example, but the pendant portion of the necklace case may allow the cord to be released, e.g., such as would be the case if the clip case 844 were to be used as the pendant portion).

FIG. 9A depicts one example of a wristband case for a portable biometric monitoring device. FIG. 9B depicts the example wristband case of FIG. 9A with a portable biometric monitoring device inserted.

In FIG. 9A, a wristband case 950 is depicted. In this particular instance, the wristband case 950 is not made primarily from a molded viscoelastic material, but is primarily made from a selection of woven materials, i.e., textiles. Some portions of the wristband case 950 may, however, be made using molding techniques and viscoelastic materials, as discussed further below.

The wristband case 950 may be sized such that the wristband case 950 may be wrapped around a wearer's forearm such that a hook region 964 of the wristband case 950 may overlap with a loop region 962 on the opposite end of the wristband case 950. The hook region 964 and the loop region 962 may feature hooks and loops, respectively, of a hook-and-loop fastener system. Of course, other techniques for closing the wristband case 950 about a person's forearm may also be used, e.g., magnetic clasps, buttons, ties, elastic loops or ties, etc. In some implementations, the wristband case 950 may be a continuous loop of material that may stretch so as to be able to be pulled over a wearer's hand and worn on the wearer's forearm.

The depicted variant is similar to a wristband sold with the Fitbit One™, which measures approximately 9.5" in length when laid flat, 2.5" in width, and approximately 0.06" in thickness. The loop region of this wristband measures approximately 4" in length, and the hook region measures approximately 0.625" in length.

As can be further seen in FIG. 9A, a pocket region 982 may be provided between the hook region 964 and the loop region 962. The pocket region 982 may include a pocket that is accessible via an opening 960. The pocket region 982 may be formed between two or more layers of material that are joined together, e.g., sewn, glued, or otherwise attached to one another, substantially about the perimeter of the pocket region 982. The pocket region 982 may also have a display window 972 that may allow an item inserted into the pocket of the pocket region 982 to be at least partially visible to a wearer of the wristband case 950. The display window 972 may include another layer of material that is sewn, glued, or otherwise attached to one of the layers of material forming pocket region 982. In the depicted example, the wristband case 950 is formed from at least three distinct layers in the pocket region—a bottom layer and a top layer both made from high-thread-count nylon or other synthetic material, and a coarser mesh fabric interposed between the bottom layer and the top layer. The top layer, as shown, has a cutout for the display window 972, and the mesh fabric is visible through the display window 972. The three fabric layers may be bonded together about the perimeter of the pocket region 982, e.g., by a neoprene layer or other elastomeric material that fuses the multiple fabric layers into a flexible fabric stack. In the depicted implementation, the inter-layer bonding only occurs around the perimeter of the pocket region 982, i.e., not in the display window 972 and not between the display window 972 and the opening 960 (although the mesh fabric is still bonded to the top layer between the display window 972 and the opening 960, the mesh fabric and the top layer are not bonded to the bottom layer in this area).

The area surrounding the opening 960 may be impregnated with an elastomeric material 968 that may prevent fraying of the fabric through which the opening 960 passes and that may also serve to locally reinforce the fabric to prevent the opening 960 from opening too much. Stress relief holes 966 may be provided at either end of the slit that forms the opening 960 to mitigate the effects of flexure of the opening 960 due to repeated insertions and removal of a biometric monitoring device 902 (as shown in FIG. 9B). As can be seen, the biometric monitoring device 902 may be inserted through the opening 960 and into the pocket within the pocket region 982, where it may be visible behind the display window 982.

While the opening 950 may be stretched to some degree, excessive stretching, e.g., sufficient to expand the opening 950 to a degree allowing the biometric monitoring device 902 to be inserted through the opening Alternatively, the device may be placed in the case by orienting it in a way which its dimensions are smaller or comparable to the opening. Once in the case, the device may be reoriented so that its dimensions along the opening are larger than the opening.

In the Fitbit One™ wristband case, the opening is approximately 1.25" in length (as compared with the approximately 1.9" length of the Fitbit One™) and the display window is approximately 2" by 1.25" in size.

It is to be understood that other implementations of a wristband case such as that shown in FIGS. 9A and 9B are also contemplated. For example, the display window may, in some implementations, be provided by a translucent contiguous material rather than by the depicted mesh. In another example, the wristband case may be provided without ventilation holes or perforations 952.

One feature shared by such alternative implementations of a textile-based wristband case, however, is that the opening may be provided by a slit in a textile layer that is oriented such that the slit is aligned with the forearm on which the wristband case is to be worn. The present inventors have realized that this is advantageous over alternative orientations, e.g., perpendicular to the forearm, since such a location makes it more difficult for a biometric monitoring device that is inserted into the pocket to accidentally work its way out of the pocket and through the opening.

Cases similar to the textile-based case of FIGS. 9A and 9B may be sized to allow such cases to be worn on any convenient part of the wearer's body, clothing, or accessories, e.g., such as a backpack, beltpack, purse, or anything else the wearer might carry or wear. In another implementation, an adhesive could be applied by the user to the back of the case and/or the attachment surface. In one implementation, the adhesive or hook and loop attachment case is disposable. This may prove advantageous in the case of a race event where the device contains performance and/or timing tracking capabilities and is recovered after the event by the event organizers. The case must be secure and non-intrusive for the race participants, but may not be desirable to recover after the event due to sanitary concerns, making a disposable adhesive case ideal. A disposable case may also prove desirable in a medical setting such as a hospital where there is a need to monitor patients but diseases which can be spread by contact with the skin must be prevented.

FIG. 10 depicts a variety of example cases which are compatible with a depicted example portable biometric monitoring device. In FIG. 10, a biometric monitoring device 1002, which is similar to the biometric monitoring device 302 of FIG. 3, may be inserted into any of the cases shown, including a clip case 1044, a keychain case 1046, a necklace case 1048, and wristband cases 1050 and 1050'. In contrast to the wristband case shown in FIGS. 9A and 9B, the wristband cases 1050 and 1050' both feature molded construction and are made from a flexible, compliant material allowing them to be wrapped around a person's forearm. As shown, the wristband cases 1050 and 1050' may, when the biometric monitoring device 1002 is inserted therein, appear similar to a watch. The wristband cases 1050 and 1050' may have opposing ends that fasten to one another using a buckle similar to that found in conventional watchbands. In other implementations, however, a different fastening system utilizing peg components may be used—such implementations are discussed later in this disclosure.

The design of the wristband cases may allow the user to change the closed circumference of the wristband cases by using an indexed clasp mechanism (similar to a watch buckle) or a hook-and-loop mechanism. Such wristband cases may use techniques similar to those already discussed herein to retain the biometric monitoring device in the wristband case, e.g., a stretchable undersized opening for insertion and removal of the biometric monitoring device. Similarly, the wristband case may use this opening, other openings, or case transparency to allow the user to see any displays or indicators of the biometric monitoring device.

Other cases, referred to herein as "band cases," similar to the wristband cases discussed herein may be designed so that they may be worn in one or multiple locations including, but not limited to, the wrist, forearm, bicep, chest, stomach, waist, ankle, calf, quadriceps, neck, forehead, and finger. A wristband case may, for example, be worn on a person's forearm, but may also, depending on the size of the person's ankle, be worn on their lower leg. There may be multiple band cases that are specific to one or a set of these locations, allowing the user to choose which one is most appropriate for an anticipated activity. In some other implementations, band cases may have a main body that receives the biometric monitoring device and may have multiple interchangeable bands that have different characteristics including but not limited to color, width, length, material, and clasp type. In some implementations, the band clasp (an example of which is the peg component discussed in this disclosure) may be removable, allowing the user to use the same clasp with multiple bands. For example, the user may have one clasp that may be used with multiple bands of varying colors.

In some implementations, the wearer would have the ability to use a band case reminiscent of that of a watch including metal clasp mechanism as seen in FIG. 10. Such a case may be preferred by the wearer for more formal wear or for wear in situations when the increased security of a buckle may be desired, e.g., during periods of strenuous activity. Additionally, the user could choose a band case made out of fabric and a hook and having a hook-and-loop closure mechanism that is more comfortable to wear. Such a band case may be more desirable to wear while sleeping.

In some implementations, band cases may use an elastic band that does not require a closure mechanism. For example, a band case may have a metal band forming a C-shape that is elastic enough for the wearer to flex the opening of the metal band such that they may place the band case over their forearm. Once released by the wearer, the metal band may return to its un-flexed state, the elasticity of the metal band may provide a force around the wrist that prevents the band from falling off (without the use of a clasp).

FIG. 11A depicts an example of a portable biometric monitoring device. FIGS. 11B and 11C depict different views of an example wristband case that may be used to house the example portable biometric monitoring device of FIG. 11A. FIG. 11D depicts an off-angle view of the example wristband case of FIGS. 11B and 11C. FIGS. 11D and 11E depict detail views of the ends of the bands of the example wristband case of FIG. 11F.

In FIG. 11A, a biometric monitoring device 1102 is shown; the depicted biometric monitoring device 1102 is similar to the biometric monitoring device 402 shown in FIG. 4A. In FIG. 11B, the biometric monitoring device 1102 is shown (visible through opening 1160) inserted into a wristband case 1150, which has a peg component 1184 having one or more pegs 1186 (in this case, two pegs 1186) inserted into one end of the wristband case 1102, e.g., the end of a strap that is part of the wristband case 1102. The pegs of the peg component 1184 may be inserted into peg holes 1190 located in an opposite end of the wristband case 1102, e.g., the end of an opposing strap that is part of the wristband case 1102, in order to secure the wristband case 1150 to a wearer's forearm.

The wristband case 1150 shown has a translucent window portion that is co-molded with the rest of the wristband case 1150 that serves as a display window 1172. The translucent window portion may completely encircle the wristband case 1102, as shown in the pictured variant, or may be located only in an area directly overlaying a display of the biometric monitoring device 1102. In the pictured implementation, the translucent window portion is made from a smoked or tinted plastic so that a wearer of the biometric monitoring device 1102/wristband case 1150 may be effectively unable to see the display of the biometric monitoring device 1150 through the display window 1172 unless the display is actually displaying content, e.g., illuminating pixels on a display or discrete LEDs.

FIGS. 11E and 11F show detail views of the ends of the wristband case 1150 shown in FIG. 11D. As can be seen, two pegs 1186 protrude from the "left" band portion of the wristband case 1150, and the "right" band portion of the wristband case has a plurality of peg holes 1190 that may be arranged in a manner that permits the pegs 1186 to be selectively engaged with a like number of peg holes 1190 so as to adjust the circumference of the wristband case 1150 to allow for a wide range of adjustability to suit differing wrist/forearm sizes. It is to be understood that the "right" and "left" descriptors, as used herein, are used to refer to the location of features with respect to their relative positioning within the drawing views and are not to be understood to limit the features to only the described locations.

The pegs may be molded plastic or metal in construction, and may generally be made from a much harder and/or stiffer material than the wristband case is (or at least the band portions of the wristband case). The pegs may be engaged with the peg holes by elastically stretching the hole openings to conform with the wider head of the protrusions. Once the peg or pegs are pushed through the band holes, the peg holes may contract again around the thinner portion of the peg geometry, thus holding the two band portions of the wristband case together at the desired circumference.

In another implementation, the pegs may be made out of a flexible material that can conform to harder and/or stiffer material in the wristband case. Alternatively, the pegs and the wristband case may both be flexible and may conform to each other to allow the head portion of the peg to be inserted through the peg hole.

The pegs 1186 may have bases that are embedded within the band portion of the wristband case 1150, or may, as in the depicted example, protrude from a base portion that is separate from the band portion (but that may be inserted into holes similar to the peg holes 1190 but are located on the band portion having the pegs 1186).

Figure 11G:
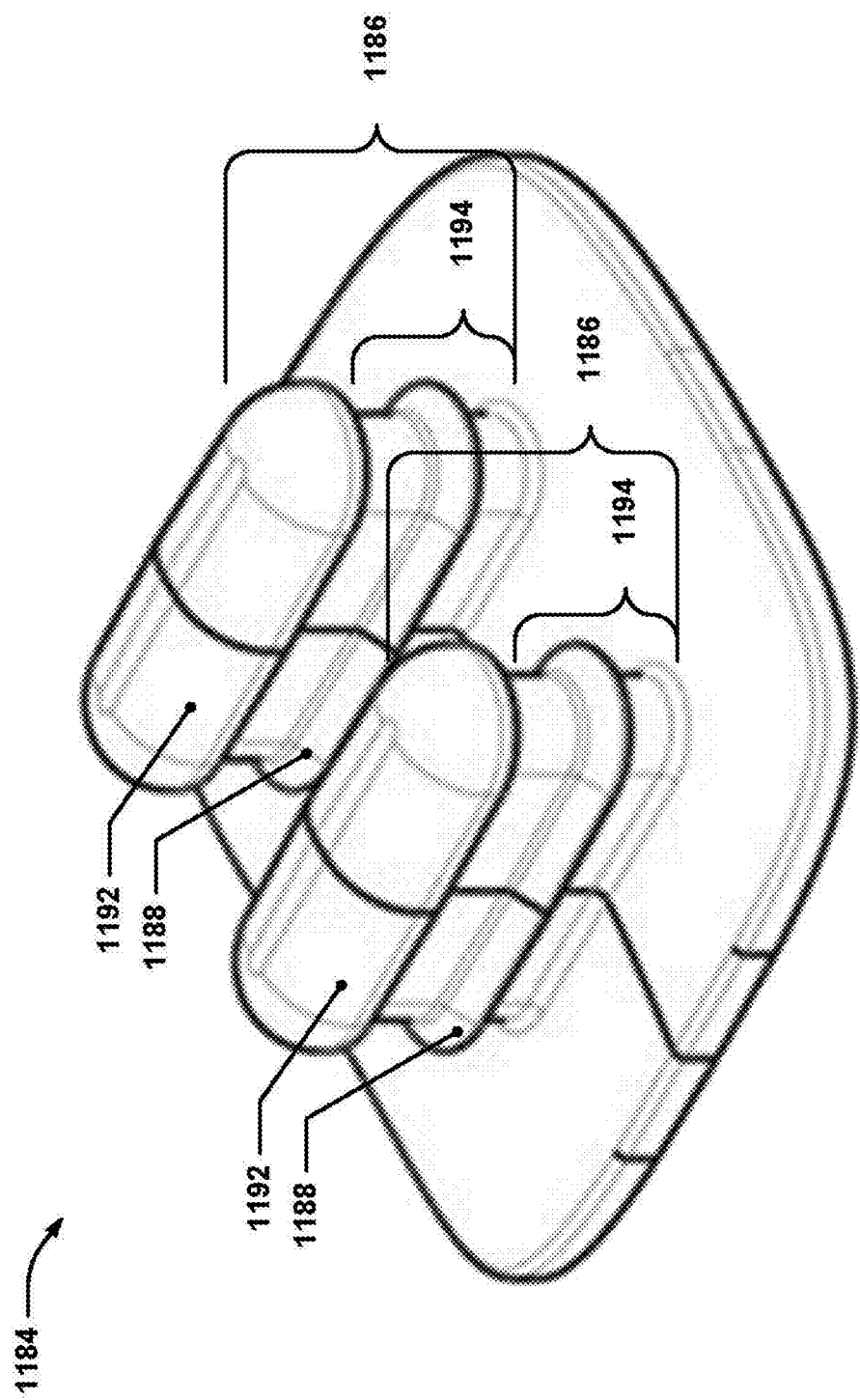
FIG. 11G depicts a detailed view of an example of a peg component.

FIG. 11G depicts a detailed view of an example of such a peg component. For example, a peg component 1184 may have a base portion that has one or more pegs 1186 protruding from it. Each peg 1186 may have a central stem 1194 or core with a head portion 1192 capping the stem 1194. The head portion 1192 may be rounded on top to allow a person pushing the head portion 1192 into a peg hole 1190 to do so with decreased difficulty as compared to hard-edged head portions. The head portion 1192 may be larger in cross-sectional area in a plane substantially parallel to the base of the peg component 1184 than the cross-sectional area of the stem 1194 of the peg 1186 in a similar plane.

In addition to the head portion 1192, the peg 1186 may have a peg rib 1188 that is located between the head portion 1192 and the peg component 1184 base. The peg rib 1188 may act to secure the peg 1186 in a hole similar to the peg holes 1190 but located on the band portion opposing the band portion having the peg holes 1190. The peg ribs 1188 may be flared, e.g., have a 90° shoulder on the side facing the peg component 1184 base, and a 45° slope on the side facing the head portion 1192. This may facilitate retention of the peg component 1184 in the band portion when the wristband case 1102 is unclasped.

FIGS. 12A through 12F depict an example biometric monitoring device and a wristband case in throughout various stages of insertion of the biometric monitoring device into the wristband case.

Figure 12C:
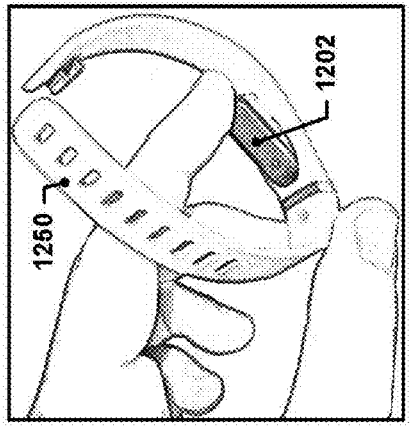
FIGS. 12A through 12F depict an example biometric monitoring device and a wristband case in throughout various stages of insertion of the biometric monitoring device into the wristband case.
Figure 12B:
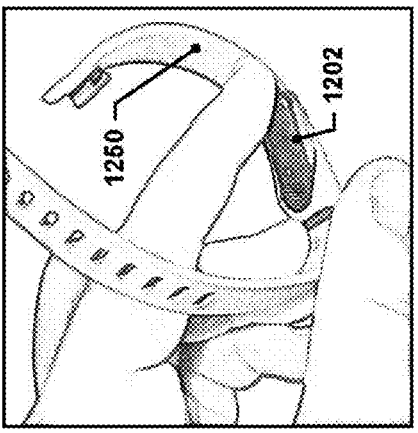
Figure 12A:
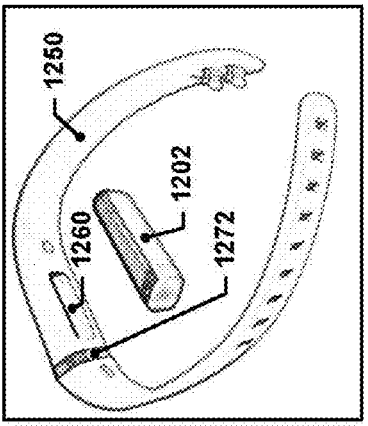

In FIG. 12A, a biometric monitoring device 1202 and a wristband case 1250 are shown. The depicted biometric monitoring device 1202 and the wristband case 1250 are similar in construction to a Fitbit Flex™. The wristband case 1250 may be a molded wristband made from a flexible elastomeric material and may have an opening 1260 in the side that faces a person's wrist when worn on the person's forearm. A display window 1272 may be embedded in the molded structure of the wristband case 1250.

In FIG. 12B, the biometric monitoring device 1202 has been partially inserted into the opening 1260. As can be seen, the opening 1260 has distended somewhat to accommodate the insertion of the biometric monitoring device 1202 since the biometric monitoring device 1202 is wider than the width of the opening in such an orientation.

In FIG. 12C, the biometric monitoring device 1202 has been inserted further into the opening 1260, and has been aligned with the long axis of the wristband case 1250.

Figure 12F:
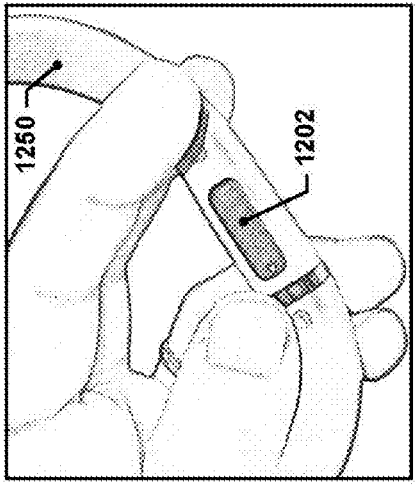
Figure 12E:
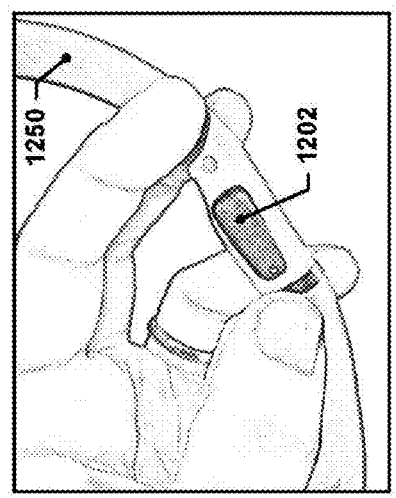
Figure 12D:
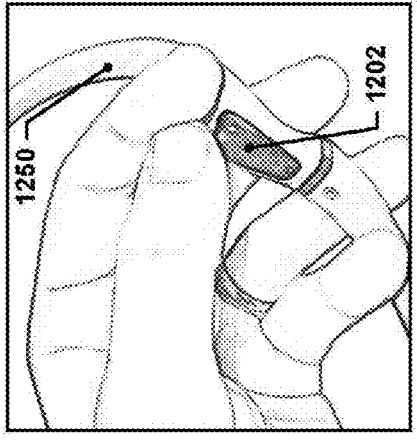

In FIG. 12D, the biometric monitoring device 1202 has been inserted as far into the opening 1260 in a direction aligned with the long axis of the wristband case 1250 as it can go. To allow the remainder of the biometric monitoring device to be inserted through the opening 1260, the wristband case 1250 is being flexed over the depicted middle finger such that the opening 1260 is elongating further in a direction aligned with the long axis.

In FIG. 12E, the biometric monitoring device 1202 has been pushed partially through the distended opening 1260. After the biometric monitoring device 1202 is pushed completely into the opening 1260, the opening 1260 may largely return to its original shape, as depicted in FIG. 12F.

Figure 12G:
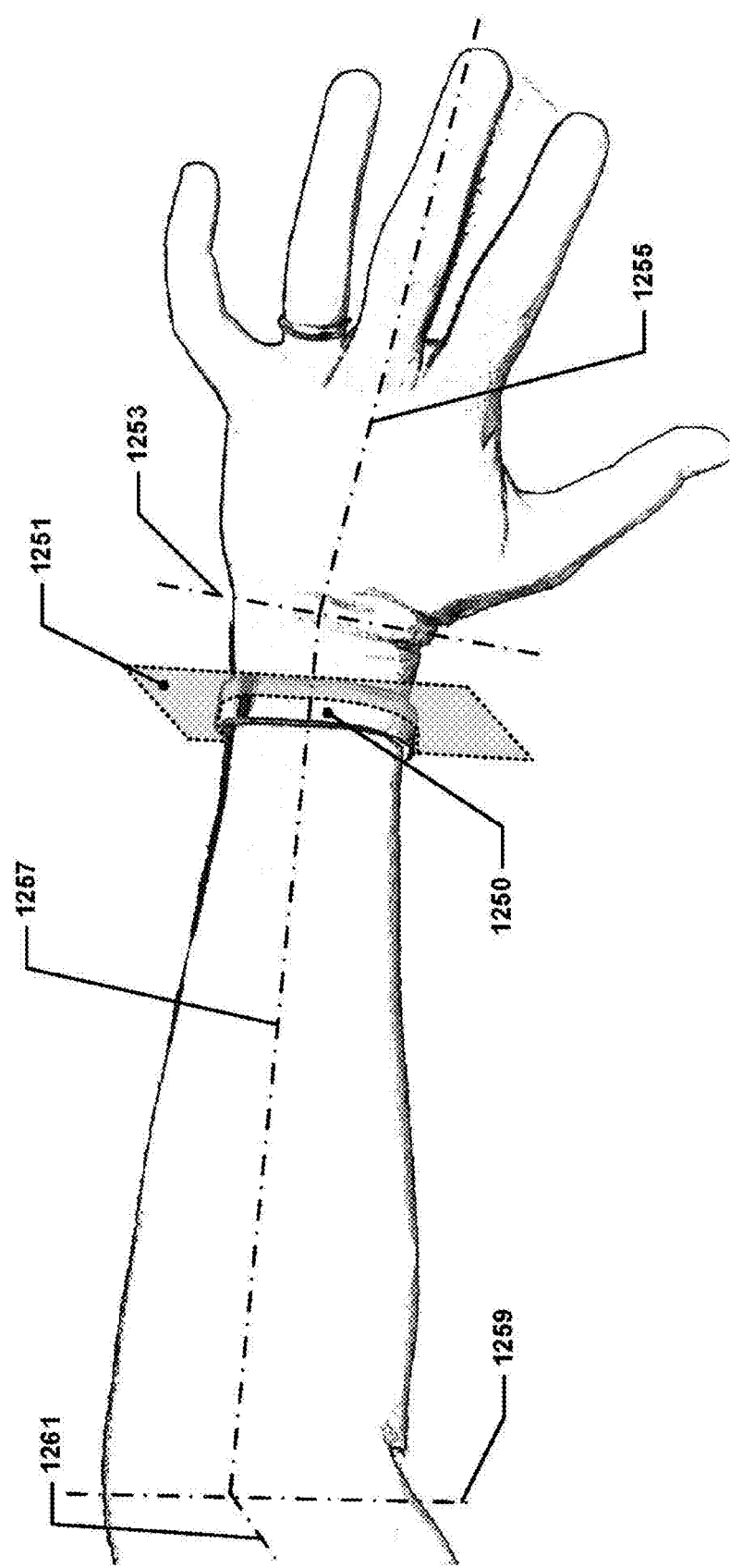
FIG. 12G depicts an example of an arm wearing a biometric monitoring device and illustrates various reference axes and planes.

FIG. 12G depicts a diagram showing the example biometric monitoring device of FIGS. 12A through 12F as worn on a person's arm. FIG. 12G may be useful as a reference frame for defining various axes and locations for future reference.

In FIG. 12G, a person's "arm" is shown. In everyday speech, the term "arm" is typically used to refer to the entirety of the limb connected to a shoulder. However, as used herein, the term "arm" refers to the portion of that limb located between the shoulder joint and the elbow joint of the limb. The term "forearm" refers to the portion of that limb between the elbow joint and the wrist joint. The forearm may encompass a portion of the limb that may often be called the "wrist," e.g., the portion of the forearm on which a person may wear a watch or bracelet. This disclosure may use the term "wristband" as commonly used in everyday speech, i.e., to indicate a band that fully or partially encircles a person's forearm near the wrist joint. In some cases, some people may choose to wear such a band at a loose enough setting that the band may slide into the wrist joint area; such bands are still considered, however, to be configured to be worn on the person's forearm within this disclosure. This disclosure uses the conventions outlined in Joseph E. Muscolino's "Kinesiology: The Skeletal System and Muscle Function," Second Edition (2011), when discussing various body parts or other kinesiological concepts.

Since a person's arm and forearm are organic structures with widely-varying appearances from person to person, it may be useful to utilize a common reference framework when discussing such a limb or when discussing items that may be worn on such a limb. For example, despite the wide variation in shape and size of forearms in the general population, every forearm will have a forearm axis 1257 that is substantially aligned with the longest direction of the forearm. Another way of thinking of the forearm axis 1257 is as the axis that passes through the nominal centers of rotation of the wrist joint and the elbow joint. In addition to a forearm axis, it may be useful to refer to an elbow axis 1259 and a wrist axis 1253. The elbow axis 1259 may generally define the pivot axis of the forearm about the elbow joint during flexion and extension of the forearm, and the wrist axis 1253 may generally define the pivot axis of the hand about the wrist joint during flexion and extension of the hand. An arm axis 1261 may be generally aligned with the long dimension of the arm and may pass through the center of rotation of the elbow joint and the center of rotation of the shoulder joint (not pictured). A hand axis 1255 may pass through the center of the wrist joint and generally in a direction aligned with the middle finger of the hand when at full extension.

As can be seen, the wristband case 1250 shown may encircle the forearm near the wrist and may generally define a wristband plane 1251 that is substantially perpendicular to the forearm axis 1257.

When the biometric monitoring device 1202 is worn in a wristband case such as wristband case 1250, the opening 1260 that is located in the "rear" of the wristband case may be blocked by the wearer's forearm, thus preventing the biometric monitoring device 1202 from being able to slip out of the wristband case 1250. In other implementations, however, the wristband case may be configured such that the opening is located in the "front" of the wristband case, e.g., facing away from the wearer's forearm.

It is to be understood that variations on the wristband cases discussed herein are also considered to be within the scope of this disclosure, e.g., band cases that are sized to be worn on other limb locations on a person. For example, a band case may be sized so as to be worn on a person's leg near the ankle joint, or on a person's arm, i.e., between the shoulder joint and the elbow joint. In some implementations, a band case may be sized so as to be worn by animals, e.g., pets such as cats and dogs. Such band cases may be worn by the pets as collars, e.g., around the pet's neck. In such implementations, the band case may generally define a band plane (similar to the wristband plane 1251) that is substantially perpendicular to the longitudinal axis of the limb or the spinal axis of the neck (depending on the location where the band case is intended to be worn). Generally speaking, a band case that is configured to be worn on an organism may refer to a band case that is configured to be worn on either a human or an animal.

Figure 13C:
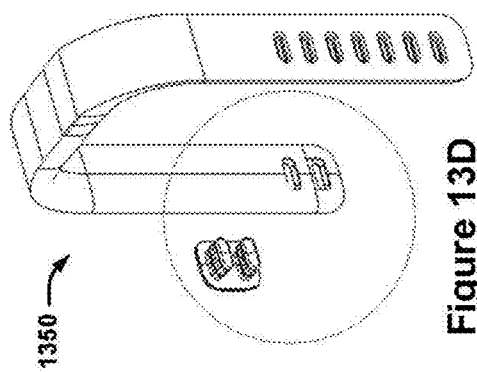
FIGS. 13C and 13D depict the example wristband case of FIG. 13A with the peg component installed and removed, respectively.
Figure 13D:
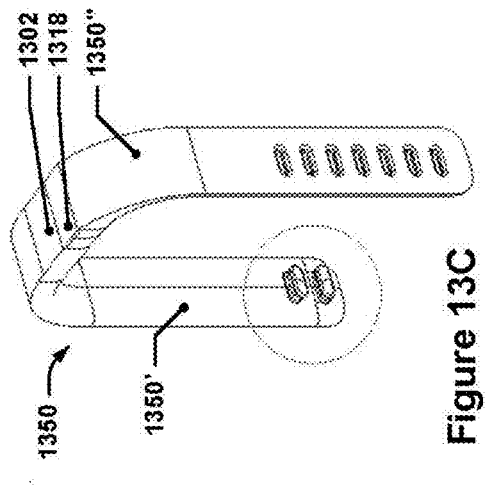
Figure 13F:
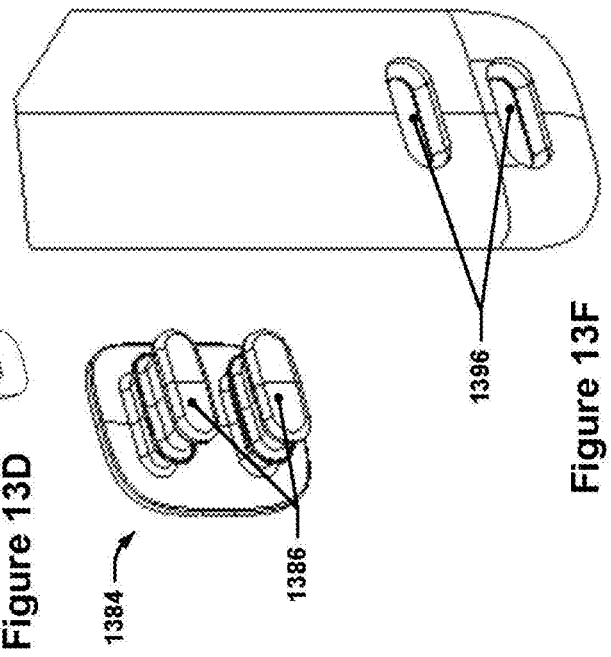
FIGS. 13E and 13F depict detail views of the peg components shown in FIGS. 13A and 13B, respectively.
Figure 13E:
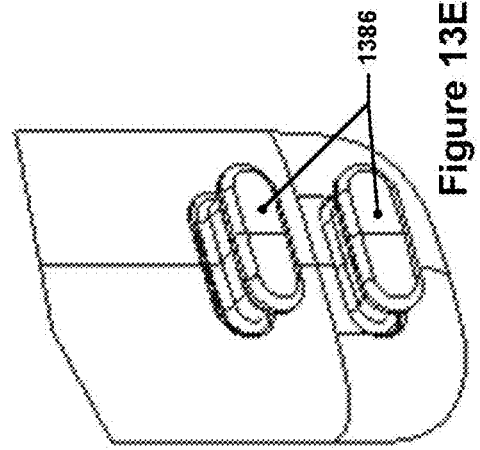

FIGS. 13A and 13B depict different off-angle views of another example of a portable biometric monitoring device. FIGS. 13C and 13D depict the example wristband case of FIG. 13 with a peg component installed and removed, respectively. FIGS. 13E and 13F depict detail views of the peg components shown in FIGS. 13A and 13B, respectively. FIGS. 13G and 13H depict exploded side views of the example portable biometric monitoring device shown in FIG. 13. FIGS. 13I and 13J depict side views of the example portable biometric monitoring device shown in FIG. 13A.

In the implementation pictured in FIGS. 13A through 13J, a biometric monitoring device 1302 is inserted into a two-part wristband case 1350. As can be seen in FIGS. 13C through 13F, the wristband case 1350 may utilize a peg component 1384 that has pegs 1386 and peg ribs 1388. The pegs 1386 may be inserted into peg component holes 1396 in one end of the wristband case 1302, as shown in FIGS. 13E and 13F.

The two-piece nature of the wristband case 1350 may be more fully understood with reference to FIGS. 13G and 13H, which depict the wristband case 1350 separated from the biometric monitoring device 1302. In the pictured implementation, the biometric monitoring device 1302 may have opposing ends, each of which is configured to be inserted into a receptacle located on a different portion of the wristband case 1350. For example, in FIG. 13G, the "left" end of the biometric monitoring device 1302 may be configured to be fully inserted into a receptacle in wristband case portion 1350', and the "right" end of the biometric monitoring device 1302 may be configured to be fully inserted into a receptacle in wristband case portion 1350". Ribs, ridges, or other features on the insertable ends of the biometric monitoring device 1302 and/or the interior surfaces of the receptacles of the wristband case portions 1350' and 1350" into which the insertable ends may be inserted may be used to prevent the wristband case portions from easily separating from the biometric monitoring device 1302. Alternatively, or additionally, the insertable ends of the biometric monitoring device 1302 may be bonded into the receptacles on the wristband case portions 1350' and 1350". FIGS. 13I and 13J depict side views of the assembled biometric monitoring device 1302/wristband case 1350.

Figure 14A:
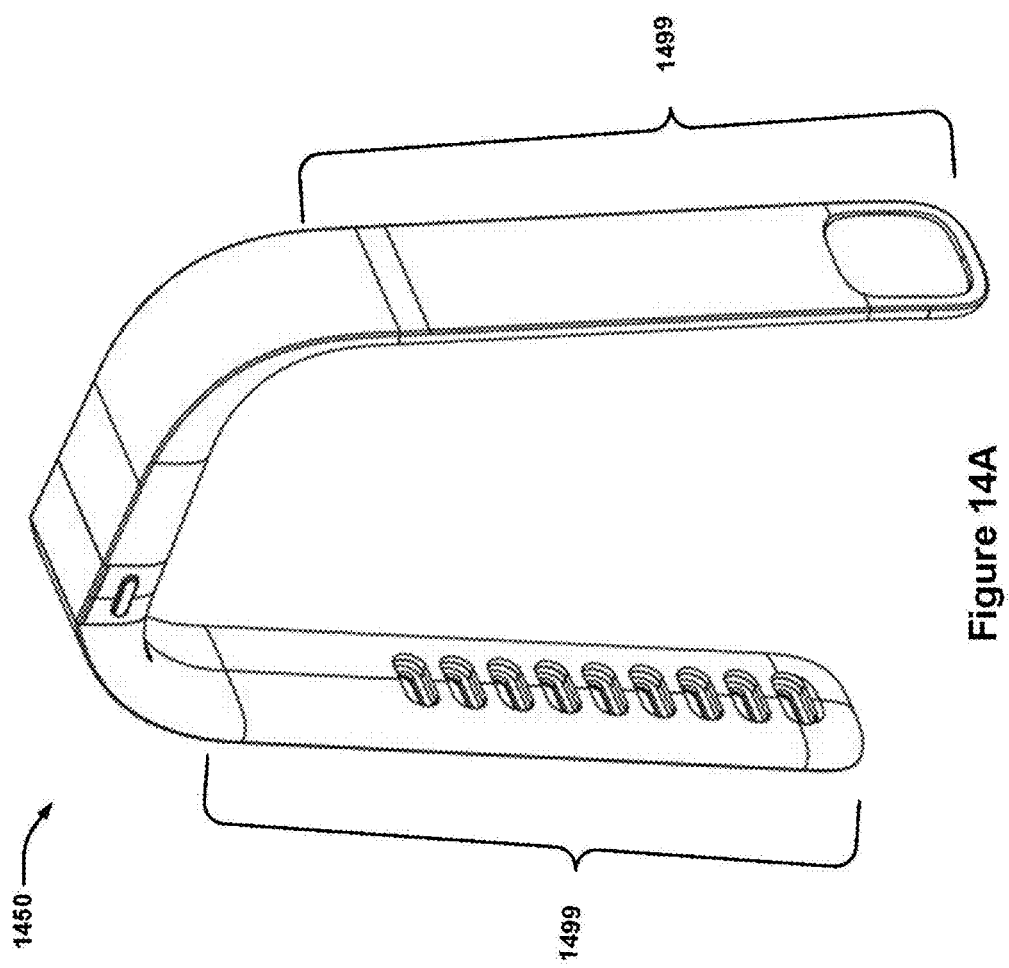
FIG. 14A depicts an example of a wristband case featuring an integrated spine component.
Figure 14B:
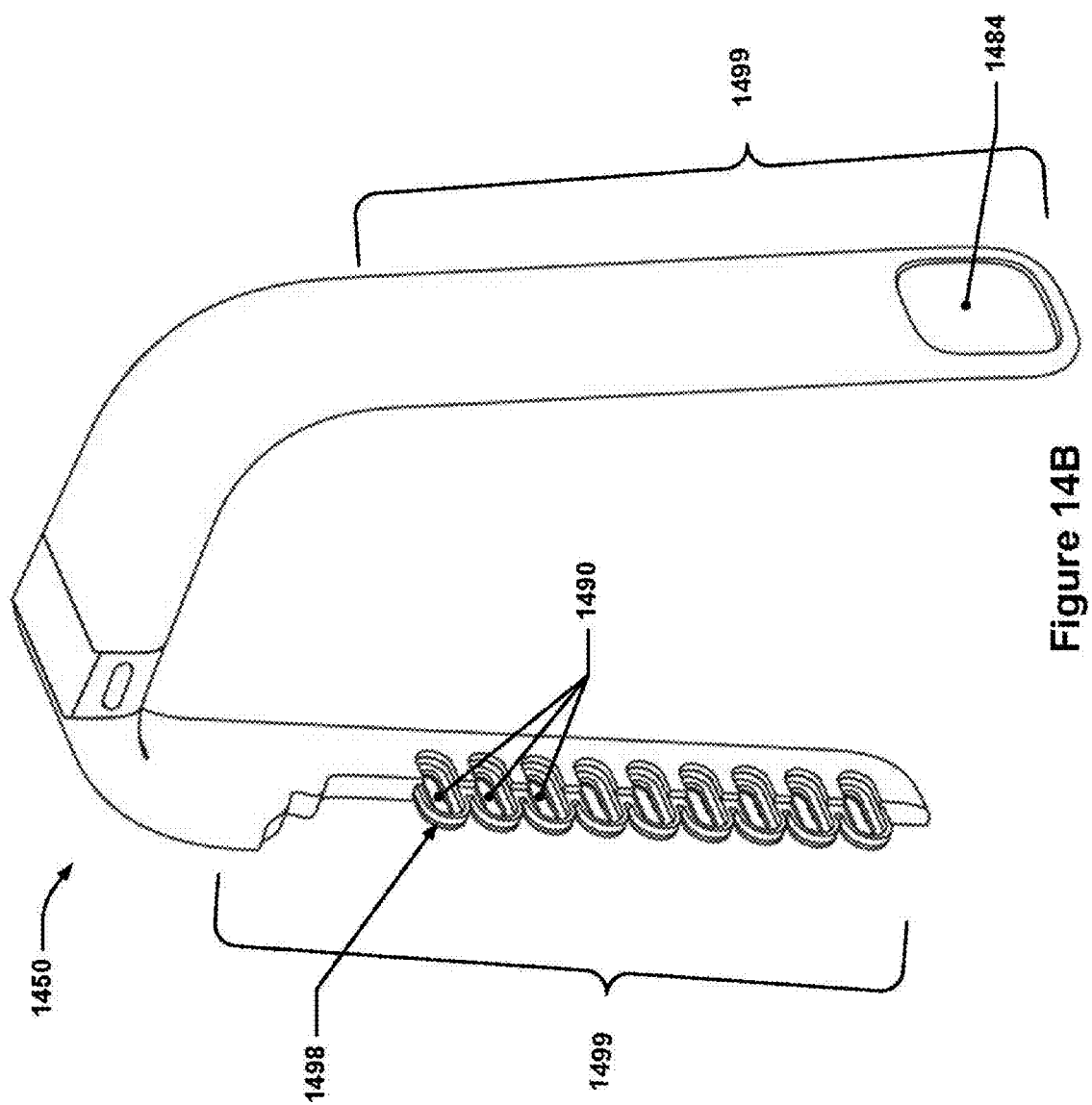
FIG. 14B depicts an off-angle view of a partial cutaway of the example wristband case having a spine component.

FIG. 14A depicts an example of a wristband case featuring an integrated spine component. FIG. 14B depicts an off-angle view of a partial cutaway of the example wristband case having a spine component.

In general, it may be desirable that the band portions 1499 of a wristband case remain flexible enough to conform to the wearer's body in order to be as comfortable as possible. One way of achieving such flexibility and comfort is to use a sufficiently soft elastomeric material to construct all or part of the band portions 1499 of a wristband case. One problem that arises, however, is that as the material hardness is decreased, e.g., as measured by a durometer, there is a corresponding decrease in the holding force that the band portions 1499 may exert on the pegs of a peg component that are inserted into peg holes in one of the band portions 1499, i.e., it is easier to pull the pegs back through softer material and out of the peg holes.

One technique for addressing such possible issues is to include a second component (herein referred to as the "spine") made from a harder material, e.g., a harder elastomer, than the rest of the band portion 1499. The spine may be either separately molded and then insert-molded inside the strap portion or molded sequentially in a double-injection type injection molding machine. The geometry of the spine may be such that the portions of the spine that may engaged with the pegs of the opposing band portion 1499 may be sized to be larger than the cross-sectional area of the peg stem and the peg head portion. Such geometry may result in the peg primarily contacting the harder spine material rather than the softer material of the band portion 1499. For example, if the pegs have a cross-section with a nominal stadium (or discorectangular) shape, i.e., a rectangle capped on two opposing sides by semicircles, the spine may, in each region around a peg hole, have a similar shape that allows the peg head portion to be inserted through the peg hole (and spine) and then rest on the spine material. Each region of the spine that surrounds a peg hole may be joined to adjacent similar regions by a smaller-width (as measured cross-wise to the band portion 1499) region of spine material so as to not greatly reduce the flexibility of the band portion 1499 while still providing for enhanced peg grip by the peg holes.

In other implementations, a band portion 1499 may contain two or more parallel spine components made from a harder elastomer than the rest of the band portion 1499. Each of these spine components may engage one or more pegs, for example, two parallel pegs. By varying the number of pegs, the force required to insert or remove the pegs can be varied by the designer.

In some implementations, harder and/or stiffer material may be incorporated into regions of the band portions 1499 other than where pegs holes are located in order to improve usability or cosmetic appearance. For example, the region of the band portion 1499 through which a peg component may be inserted (the band portion 1499 opposite the band portion 1499 with the peg holes) may be surrounded by harder, stiffer material to facilitate the insertion of the pegs into peg holes without needing to press directly on the peg component.

This construction allows the designer to tune the material characteristics of the band portion 1499 and the mechanics of peg/peg hole insertion separately without unduly compromising the cosmetic appearance and/or comfort of the strap assembly.

Figure 14C:
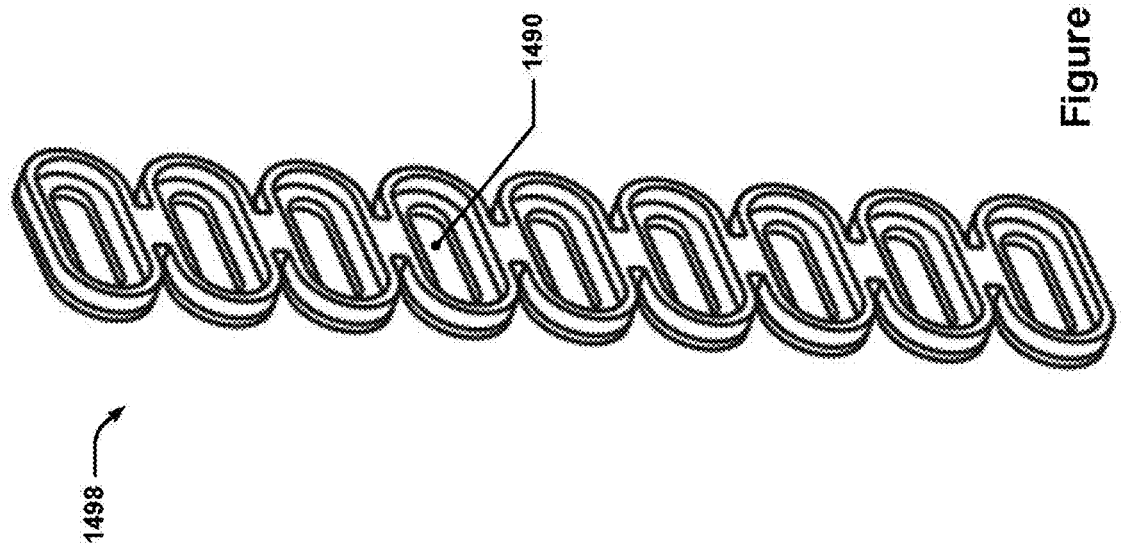
FIG. 14C depicts an example of a spine component that may be incorporated into a strap or band.

In FIGS. 14A and 14B, a wristband case 1450 is shown. The wristband case 1450 may house a biometric monitoring device 1402. In this example, the wristband case 1450 and the biometric monitoring device 1402 are similar to the wristband case 1350 and the biometric monitoring device 1302, although the spine component discussed may be used with any of a variety of different molded wristband designs, e.g., molded wristband design such as those discussed earlier in this disclosure. As noted above, FIG. 14B depicts a partial cutaway of the wristband case 1450, exposing a spine component 1498 to view. The spine component 1498 may be made of a stiffer, less flexible material than the remainder of the wristband case 1450, and may be embedded or encapsulated within the remainder of the wristband case 1450. The spine component 1498 may be nearly entirely embedded aside from portions of the spine component in the vicinity of each peg hole 1490. Thus, pegs (not shown) protruding from peg component 1484 may engage with the spine component 1498 when inserted into the peg holes 1490. FIG. 14C depicts an example of a spine component that may be incorporated into a strap or band.

FIG. 14D depicts a cross-section of an example of a spine co-molded into a strap, and FIG. 14E depicts a detail view of the cross-section of FIG. 14D. As can be seen, the spine component may have a series of apertures through it that correspond to the peg holes 1490. The spine component 1490 may locally reinforce the wristband case 1450 and prevent tearing or other damage to the more resilient/compliant materials used in the wristband case 1450.

In the various implementations described herein, the case may have a feature which identifies itself to the biometric monitoring device or a secondary device, e.g., a smartphone paired with the biometric monitoring device. For example a wristband case may have an NFC tag which can be read by an NFC communications interface of the biometric monitoring device (or smartphone paired with such a device). Other identifying features may include an RFID tag, other wireless communications technologies (passive or active), a magnet, or circuitry electrically connected to the device. The biometric monitoring device may change its functionality depending on the case identifier. For example, a wristband case identifier may cause data obtained by the biometric monitoring device to be interpreted with respect to a framework based on the assumption that the biometric monitoring device is located on a person's forearm near their wrist. This change in functionality could include a change in algorithm of counting steps if the device were to include a pedometer and/or the display of the time. In another implementation, the wristband may contain a magnet on one side of the band whose position can be measured by a magnetometer in the device and used correct the orientation of the display.

Other implementations regarding the use of short range wireless communication are described in U.S. patent application Ser. No. 13/785,904, titled "Near Field Communication System, and Method of Operating Same" filed Mar. 5, 2013 which is entirely incorporated herein by reference.

Generally speaking, the above-discussed cases may have channels, vents, and/or windows in them to allow a pressure transducer or altimeter in or on the device housing to be exposed to the ambient pressure, e.g., water or air pressure, in the vicinity of the biometric monitoring device. Examples of such channels, vents, or windows may be found in ventilation holes 652 of FIG. 6A and ventilation holes 1352 in FIGS. 13H and 13J. In one implementation, one or more pressure channels allow air pressure to travel from the side of the bottom of the band to one or more pressure vents on the bottom of the biometric monitoring device. These vents may use a gas-permeable, liquid-impermeable (or at least liquid-resistant) membrane such as a Gore™ vent to allow a pressure sensor in the interior of the biometric monitoring device to measure ambient air pressure without letting liquid into the interior of the biometric monitoring device.

There are many inventions described and illustrated herein. While certain implementations, features, attributes and advantages of the inventions have been described and illustrated, it should be understood that many others, as well as different and/or similar implementations, features, attributes and advantages of the present inventions, are apparent from the description and illustrations. As such, the above implementations of the inventions are merely exemplary. They are not intended to be exhaustive or to limit the inventions to the precise forms, techniques, materials and/or configurations disclosed. Many modifications and variations are possible in light of this disclosure. It is to be understood that other implementations may be utilized and operational changes may be made without departing from the scope of the present inventions. As such, the scope of the inventions is not limited solely to the description above because the description of the above implementations has been presented for the purposes of illustration and description.

Importantly, the present invention is neither limited to any single aspect nor implementation, nor to any combinations and/or permutations of such aspects and/or implementations. Moreover, each of the aspects of the present invention, and/or implementations thereof, may be employed alone or in combination with one or more of the other aspects and/or implementations thereof. For the sake of brevity, many of those permutations and combinations will not be discussed and/or illustrated separately herein.

What is claimed is:

1. A band configured to be worn on a person's limb, the band comprising:
    a biometric monitoring device with a first end and a second end;
    a first molded body made of a first compliant material, wherein a first cavity of the first molded body is configured to receive the first end of the biometric monitoring device, wherein the first end of the biometric monitoring device is bonded into the first cavity;
    a second molded body made of a second compliant material, wherein a second cavity of the second molded body is configured to receive the second end of the biometric monitoring device, wherein the second end of the biometric monitoring device is bonded into the second cavity; and
    a first hole that passes through the first molded body, wherein:
        the first molded body and the second molded body are flexible and connectable together to form a band.

2. The band of claim 1, wherein the first end of the biometric monitoring device is curved towards the person's limb when the biometric monitoring device is worn on the person's limb.

3. The band of claim 1, wherein the second end of the biometric monitoring device extends substantially linearly outward before curving towards the person's limb at the end.

4. The band of claim 1, the biometric monitoring device further comprising a substantially rectangular cross-section between the first end and the second end.

5. The band of claim 4, wherein the corners of the rectangular cross-section have rounded radii.

6. The band of claim 5, wherein the two corners of the rectangular cross-section closer towards the person's limb when the biometric monitoring device is worn on the person's limb have larger radii than the two corners of the rectangular cross-section farther away from the person's limb.

7. The band of claim 1, the biometric monitoring device further comprising a digital display including a display window and a luminous display inside the display window, wherein at least a portion of the luminous display is visible through the display window.

8. The band of claim 7, wherein the display window is tinted.

9. The band of claim 8, wherein the luminous display is transiently visible through the display window only when the luminous display is illuminated.

10. The band of claim 1, wherein the first end is bonded into the first cavity by way of an adhesive.

11. The band of claim 1, wherein the second end is bonded into the second cavity by way of an adhesive.

12. The band of claim 1, wherein at least one of the first cavity, the second cavity, the first end, and the second end includes one or more features selected from the group consisting of ribs and ridges.

13. The band of claim 1, wherein the first end includes mechanical features configured such that when the first cavity receives the first end, the mechanical features prevent the first end from easily separating from the first cavity.

14. The band of claim 1, wherein the first compliant material and the second compliant material are the same material.

15. The band of claim 1, further comprising a spine, wherein:
    the spine is made of a third compliant material;
    the spine includes a third hole that passes through the spine; and
    the first molded body is molded around the spine such that the third hole is aligned with the first hole and the spine is encased within the first molded body.

16. The band of claim 15, wherein the third compliant material is harder, as measured by a durometer, than at least one of the first compliant material and the second complaint material.

17. The band of claim 1, further comprising a second hole that passes through the second molded body.

18. The band of claim 1, further comprising an additional N holes that pass through the first molded body, where N is an integer greater than or equal to 1.

19. The band of claim 17, further comprising an additional N holes that pass through the second molded body, where N is an integer greater than or equal to 1.

20. The band of claim 1, further comprising a ventilation hole in the first molded body, the ventilation hole configured to fluidically connect a pressure vent for a pressure sensor in the first end to an ambient environment adjacent to an exterior surface of the first molded body when the first end is bonded into the first cavity.

21. The band of claim 1, further comprising a peg component, the peg component configured to be inserted into the first hole.

22. The band of claim 17, further comprising a peg component, the peg component configured to be inserted into the first hole and/or the second hole.

23. The band of claim 1, wherein at least one of the first compliant material and the second compliant material is an elastomeric material.

24. The band of claim 1, wherein at least one of the first compliant material and the second compliant material has an elastic moduli of between 1 to 690 megapascal.

25. The band of claim 21, wherein the peg component is molded plastic in construction.

26. The band of claim 21, wherein the peg component is metal in construction.

27. The band of claim 21, wherein the peg component includes one peg.

28. The band of claim 21, wherein the peg component includes two or more pegs.

29. A band configured to be worn on a person's limb, the band comprising:
- a biometric monitoring device with a first end and a second end;
- a molded band made of a compliant material, wherein;
  - the molded band is comprised of a first molded part and a second molded part,
  - the first molded part includes a first cavity configured to receive the first end of the biometric monitoring device and the first end of the biometric monitoring device is bonded into the first cavity, and
  - the second molded part includes a second cavity configured to receive the second end of the biometric monitoring device and the second end of the biometric monitoring device is bonded into the second cavity; and
- a first hole that passes through the molded band.

30. A band configured to be worn on a person's limb, the band comprising:
- a biometric monitoring device with a first end and a second end;
- a first molded body made of a first compliant material, wherein a first cavity of the first molded body is configured to receive the first end of the biometric monitoring device and hold the biometric monitoring device substantially fixed with respect to the first molded body via a bonded connection;
- a second molded body made of a second compliant material, wherein a second cavity of the second molded body is configured to receive the second end of the biometric monitoring device and hold the biometric monitoring device substantially fixed with respect to the second molded body via a bonded connection;
- a first hole that passes through the first molded body; and
- a peg component, the peg component configured to be inserted into the first hole.

* * * * *